US012740835B2

(12) United States Patent
Zhao et al.

(10) Patent No.: US 12,740,835 B2
(45) Date of Patent: Sep. 22, 2026

(54) SYSTEMS AND METHODS FOR ROBOTIC ENDOSCOPE WITH INTEGRATED TOOL-IN-LESION-TOMOSYNTHESIS

(71) Applicant: Noah Medical Corporation, San Carlos, CA (US)

(72) Inventors: Tao Zhao, Sunnyvale, CA (US); Zhongming Shen, Sunnyvale, CA (US); Nickolas Simon Saba, San Carlos, CA (US)

(73) Assignee: Noah Medical Corporation, San Carlos, CA (US)

( * ) Notice: Subject to any disclaimer, the term of this patent is extended or adjusted under 35 U.S.C. 154(b) by 102 days.

(21) Appl. No.: 18/956,330

(22) Filed: Nov. 22, 2024

(65) Prior Publication Data

US 2025/0082416 A1 Mar. 13, 2025

Related U.S. Application Data

(63) Continuation of application No. PCT/US2023/023542, filed on May 25, 2023.

(Continued)

(51) Int. Cl.
*A61B 34/00* (2016.01)
*A61B 34/20* (2016.01)

(52) U.S. Cl.
CPC ...... *A61B 34/25* (2016.02); *A61B 2034/2055* (2016.02)

(58) Field of Classification Search
CPC . A61B 34/25; A61B 2034/2055; A61B 6/547; A61B 2034/301; A61B 6/025;

(Continued)

(56) References Cited

U.S. PATENT DOCUMENTS 6,188,355 B1 2/2001 Gilboa
7,233,820 B2 6/2007 Gilboa (Continued)

FOREIGN PATENT DOCUMENTS

WO WO-2000010456 A1 3/2000
WO WO-2001067035 A1 9/2001

(Continued)

OTHER PUBLICATIONS

PCT/US2023/023542 International Preliminary Report on Patentability dated Dec. 12, 2024.

(Continued)

*Primary Examiner* — Amal Aly Farag
(74) *Attorney, Agent, or Firm* — Wilson Sonsini Goodrich & Rosati

(57) ABSTRACT

A robotic endoscopic system and method confirm whether a tool has reached a target region within a subject using tomosynthesis. While the tool is advanced into the target region, a fluoroscopic imager acquires a plurality of images, and a three-dimensional (3D) fluoroscopic image is reconstructed from the plurality of images. A first slice is identified from the 3D fluoroscopic image in which the target region is in focus and a second slice is identified in which the tool is in focus, and a depth coordinate is determined for each. A difference between the coordinates is compared with a threshold derived from a dimension of the target region to determine, in a quantitative manner, whether the tool is positioned within the target region.

15 Claims, 21 Drawing Sheets

Related U.S. Application Data

(60) Provisional application No. 63/347,203, filed on May 31, 2022.

(58) Field of Classification Search
CPC ... A61B 6/12; A61B 6/4441; A61B 2090/376; A61B 90/37; A61B 34/37; A61B 34/20; A61B 2034/2065; A61B 2034/2068
See application file for complete search history.

(56) References Cited

U.S. PATENT DOCUMENTS

| | | | | |
|---|---|---|---|---|
| 7,794,396 | B2 | 9/2010 | Gattani et al. | |
| 8,467,589 | B2 | 6/2013 | Averbuch et al. | |
| 8,565,858 | B2 | 10/2013 | Gilboa | |
| 9,033,576 | B2 | 5/2015 | Yankelevitz et al. | |
| 9,044,254 | B2 | 6/2015 | Ladtkow et al. | |
| 9,247,922 | B2 | 2/2016 | Tsujita | |
| 11,278,357 | B2 | 3/2022 | Ummalaneni | |
| 11,282,251 | B2 | 3/2022 | Merlet et al. | |
| 11,419,481 | B2 | 8/2022 | Inoue | |
| 2009/0137952 | A1 | 5/2009 | Ramamurthy et al. | |
| 2010/0022871 | A1 | 1/2010 | De Beni et al. | |
| 2011/0085720 | A1 | 4/2011 | Averbuch | |
| 2012/0046521 | A1 | 2/2012 | Hunter et al. | |
| 2012/0289777 | A1 | 11/2012 | Chopra et al. | |
| 2013/0303887 | A1 | 11/2013 | Holsing et al. | |
| 2014/0046315 | A1 | 2/2014 | Ladtkow et al. | |
| 2015/0042643 | A1 * | 2/2015 | Shibata | A61B 6/022 345/419 |
| 2015/0265368 | A1 | 9/2015 | Chopra et al. | |
| 2015/0327940 | A1 | 11/2015 | Inoue et al. | |
| 2016/0183841 | A1 | 6/2016 | Duindam et al. | |
| 2017/0035379 | A1 | 2/2017 | Weingarten et al. | |
| 2017/0035380 | A1 | 2/2017 | Barak et al. | |
| 2018/0010961 | A1 | 1/2018 | Masumura | |
| 2019/0239961 | A1 | 8/2019 | Birenbaum et al. | |
| 2019/0254649 | A1 | 8/2019 | Walters et al. | |
| 2019/0298451 | A1 * | 10/2019 | Wong | A61B 1/05 |
| 2020/0100649 | A1 | 4/2020 | Inoue | |
| 2020/0100855 | A1 | 4/2020 | Leparmentier et al. | |
| 2020/0107877 | A1 | 4/2020 | Koblish et al. | |
| 2021/0052240 | A1 | 2/2021 | Weingarten et al. | |
| 2021/0113276 | A1 | 4/2021 | Birenbaum et al. | |
| 2021/0267440 | A1 | 9/2021 | Lin et al. | |
| 2021/0338039 | A1 | 11/2021 | Koizumi | |
| 2021/0379332 | A1 | 12/2021 | Komp et al. | |

FOREIGN PATENT DOCUMENTS

| | | | |
|---|---|---|---|
| WO | WO-2019231990 | A1 | 12/2019 |
| WO | WO-2021127475 | A1 | 6/2021 |
| WO | WO-2023235224 | A1 | 12/2023 |

OTHER PUBLICATIONS

PCT/US2023/023542 International Search Report and Written Opinion dated Aug. 15, 2023.
EP23816594.8 Extended European Search Report dated Apr. 22, 2026.
U.S. Appl. No. 19/569,098 Office Action dated Jul. 29, 2026.

* cited by examiner

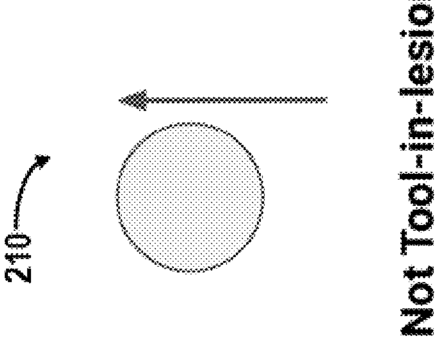
FIG. 2
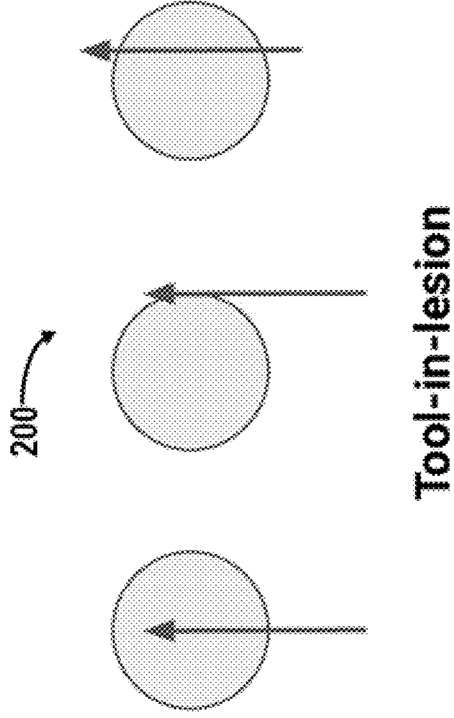

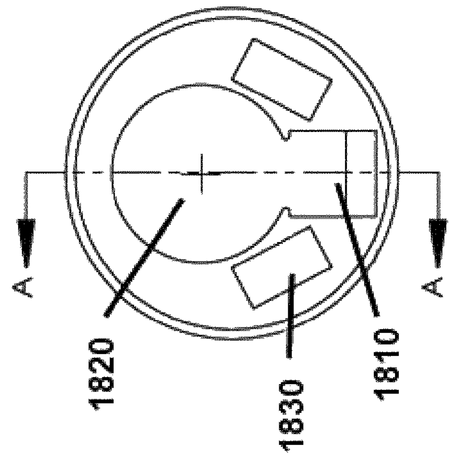
A
A
1820
1830
1810
FIG. 18
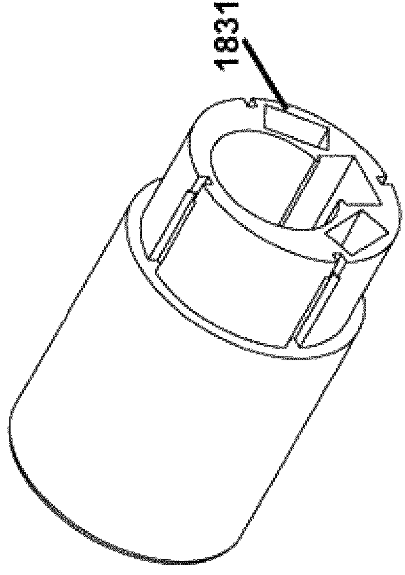
1831

SYSTEMS AND METHODS FOR ROBOTIC ENDOSCOPE WITH INTEGRATED TOOL-IN-LESION-TOMOSYNTHESIS

CROSS-REFERENCE

This application is a continuation of International Application No. PCT/US2023/023542, filed May 25, 2023, which claims priority to U.S. Provisional Patent Application No. 63/347,203, filed on May 31, 2022, which is entirely incorporated herein by reference.

BACKGROUND OF THE INVENTION

Early diagnosis of lung cancer is critical. Lung cancer remains the deadliest form of cancer with over 150,000 deaths per year. Compared to CT guided TTNA (CT-TTNA), navigational bronchoscopy has a better safety profile (less risk of pneumothorax, life threatening bleeding and length of stay) and the ability to stage the mediastinum but is associated with a lower diagnostic yield. The endoscopy (e.g., bronchoscopy) may involve accessing and visualizing the inside of a patient's lumen (e.g., airways) for diagnostic and/or therapeutic purposes. During a procedure, a flexible tubular tool such as, for example, an endoscope, may be inserted into the patient's body and an instrument can be passed through the endoscope to a tissue site identified for diagnosis and/or treatment.

Robotic bronchoscopy systems have gained interest for the biopsy of peripheral lung lesions. Robotic platforms offer superior stability, distal articulation, and visualization over traditional pre-curved catheters. Some of the traditional robotic bronchoscopy systems utilize shape sensing technology (SS) for guidance. SS catheter has an embedded fiberoptic sensor that measures the shape of the catheter several hundred times a minute. Other traditional robotic bronchoscopy systems incorporate direct visualization, optical pattern recognition and geopositional sensing (OPRGPS) for guidance. Both SS and OPRGPS systems utilize a pre-planning CT scan to create an electronically generated virtual target. However, SS and OPRGPS systems are prone to CT-to-body divergence (CT2BD). CT2BD is the discrepancy of the electronic virtual target and the actual anatomic location of the peripheral lung lesion. CT2BD can occur for a variety of reasons including atelectasis, neuromuscular weakness due to anesthesia, tissue distortion from the catheter system, bleeding, ferromagnetic interference, and perturbations in anatomy such as pleural effusions. Neither the SS system nor the OPRGPS platform has intra-operative real time correction for CT2BD. In particular, CT2BD can increase the length of the procedure, frustrate the operator and ultimately lead a nondiagnostic procedure.

SUMMARY

Digital tomosynthesis algorithms have been recently introduced for the correction of CT2BD. Tomosynthesis is limited angle tomography in contrast to full-angle (e.g., 180 degree tomography). However, tomosynthesis reconstruction does not have uniform resolution. The resolution is the poorest in the depth direction. The standard way to show a 3D volume dataset by three orthogonal planes (e.g., axial, sagittal and coronal) is ineffective since two of the planes have poorer resolution. For instance, traditional tomosynthesis applied in pulmonology has poor depth resolution (e.g., anterior-posterior (AP)) causing difficulty in determining whether a tool is within a target region (e.g., lesion). A common way to view tomosynthesis volume is to scroll in the depth direction where each slice has good resolution. In the case of pulmonology, a user may view the lesion and needle in the coronal plane and may manually scroll through the slices in the anterior-posterior (AP) direction to identify the special relationship between the needle and the lesion. Yet such processes may cause difficulty in determining the spatial relationship of the structures in the depth direction due to the tedious manual process and human error. In particular, it can be challenging to determine whether a thin tool (e.g., biopsy needle) is inside a lesion in the AP direction of a tomosynthesis reconstruction with high confidence and accuracy.

A need exists for methods and systems capable of determining whether a tool is within a target region (e.g., lesion) with improved accuracy and correctness. The present disclosure addresses the above needs by providing a method and system for tomosynthesis-based tool-in-lesion decision. In particular, the method herein provides user with quantitative information of a spatial relationship of a thin tool (e.g., needle) and a target region (e.g., lesion) in the depth direction. The methods and systems herein may identify the positional relationship of the tool and the lesion (in the depth direction) by identifying their depth separately and determine whether the (thin) tool is within the lesion in a quantitative manner. The term "thin tool" as utilized herein may refer to at least a portion of the tool (e.g., distal tip) having a dimension of no greater than 1 mm, 2 mm, 3 mm, 4 mm, 5 mm, 6 mm, 7 mm, 8 mm, 9 mm, or 10 mm.

The method herein may be applied after a robotic platform is set up, target lesions are identified and segmented, an airway registration is performed, and an individual target lesion is selected. The robotic system herein may utilize integrated tomosynthesis to improve lesion visibility and tool-in-lesion confirmation. For instance, during operation, when an endoscope is navigated through an airway to reach a target, the tool-in-lesion mode may be activated to verify if a thin tool (e.g., needle passed through a working channel of the endoscope) is within the target or not. An endoscopy navigation system may use different sensing modalities (e.g., camera imaging data, electromagnetic (EM) position data, robotic position data, etc). In some cases, the navigation approach may depend on an initial estimate of where the tip of the endoscope is with respect to the airway to begin tracking the tip of the endoscope. Some endoscopy techniques may involve a three-dimensional (3D) model of a patient's anatomy (e.g., CT image), and guide navigation using an EM field and position sensors.

In some cases, 3D image of a patient's anatomy may be taken one or more times for various purposes. For instance, prior to a medical procedure, 3D model of a patient anatomy may be created to identify the target location. In some cases, the precise alignment (e.g., registration) between the virtual space of the 3D model, the physical space of the patient's anatomy represented by the 3D model, and the EM field may be unknown. As such, prior to generating a registration, endoscope positions within the patient's anatomy cannot be mapped with precision to corresponding locations within the 3D model. In another instance, during surgical operation, 3D imaging may be performed to update/confirm the location of the target (e.g., lesion) in the case of movement of the target issue or lesion. In some cases, to assist with reaching the target tissue location, the location and movement of the medical instruments may be registered with intra-operative images of the patient anatomy. With the image-guided instruments registered to the images, the instruments may navigate natural or surgically created passageways in anatomical systems such as the lungs, the colon, the intestines, the kidneys, the heart, the circulatory system, or the like. In some instances, after the medical instrument (e.g., needle, endoscope) reaches the target location or after a surgical operation is completed, 3D imaging may be performed to confirm the instrument or operation is at the target location.

In some cases, fluoroscopic imaging systems may be used to determine the location and orientation of medical instruments and patient anatomy within the coordinate system of the surgical environment. In order for the imaging data to assist in correctly localizing the medical instrument, the coordinate system of the imaging system may be needed for reconstructing the 3D model. As described above, multiple 2D fluoroscopy images acquired at different orientations/angles may be used to create tomosynthesis or Cone Beam CT (CBCT) reconstruction to better visualize and provide 3D coordinates of the anatomical structures. However, traditional tomosynthesis has poor depth resolution (AP direction) causing difficulty in determining whether a tool is within a target region (e.g., lesion). Systems and methods herein beneficially provide tool-in-lesion confirmation in a quantitative manner thereby improving the accuracy and correctness of localizing the tool (e.g., needle) with respect to the target region.

In an aspect, a method for navigating a robotic endoscopic apparatus is provided. The method comprises: (a) navigating the robotic endoscopic apparatus to a target region inside of a body part; (b) acquiring one or more fluoroscopic images using a fluoroscopic imager when a tool is extended through the robotic endoscopic apparatus into the target region, and reconstructing a 3D fluoroscopic image based on the one or more fluoroscopic images; (c) identifying a first slice with a first coordinate corresponding to a center of the target region in the depth direction, and identifying a second slice with a second coordinate corresponding to the tool in the depth direction; and d) determining whether the tool is inside the target region based at least in part on a comparison of a difference between the first coordinate and the second coordinate to a threshold.

In a related yet separate aspect, a non-transitory computer-readable storage medium including instructions that, when executed by one or more processors, cause the one or more processors to perform operations. The operations comprise: a) navigating the robotic endoscopic apparatus to a target region inside of a body part; b) acquiring one or more fluoroscopic images using a fluoroscopic imager when a tool is extended through the robotic endoscopic apparatus into the target region, and reconstructing a 3D fluoroscopic image based on the one or more fluoroscopic images; c) identifying a first slice with a first coordinate corresponding to a center of the target region in a depth direction, and identifying a second slice with a second coordinate corresponding to the tool in the depth direction; and d) determining whether the tool is inside the target region based at least in part on a comparison of a difference between the first coordinate and the second coordinate to a threshold.

In some embodiments, the target region is a lesion that is visible in the 3D fluoroscopic image. In some cases, the first slice is identified by i) displaying the 3D fluoroscopic image within a graphical user interface (GUI), ii) selecting the first slice from a stack of slices when the lesion is in focus. In some instances, the second slice is identified when the tool is in focus. In some cases, the threshold is determined based at least in part on a dimension of the lesion. For example, the dimension of the lesion is calculated based at least in part on a 3D model of the lesion obtained from an image acquired prior to (a).

In some embodiments, the first slice or second slice is automatically identified based on a sharpness metric or contrast metric of each slice in the depth direction. In some cases, the method further comprises displaying the 3D fluoroscopic image within a graphical user interface (GUI) and displaying an overlay of the lesion on each slice from a plurality of stacks in the depth direction. In some instances, the overlay is generated based at least in part on a 3D model of the lesion intersecting each slice. The method may further comprises determining whether the tool is inside the target region by identifying whether the overlay of the lesion appears in the second slice.

In some embodiments, method may further comprises displaying, on a graphical user interface (GUI), the 3D fluoroscopic image, a first graphical visual indicator representing the first coordinate and a second graphical visual indicator representing the second coordinate.

In some embodiments, the 3D fluoroscopic image is reconstructed based on a pose of the fluoroscopic imager. In some cases, the pose of the fluoroscopic imager is estimated based on markers contained in the acquired one or more fluoroscopic images. In some cases, the pose of the fluoroscopic imager is obtained based on location sensor data. In some embodiments, the threshold comprises a margin and wherein the margin is determined based on empirical data.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2 schematically illustrates examples of tool-in-lesion and not tool-in-lesion.

FIG. 18 shows an example distal portion of the catheter with integrated imaging device and the illumination device.

DETAILED DESCRIPTION OF THE INVENTION

Figure 1:
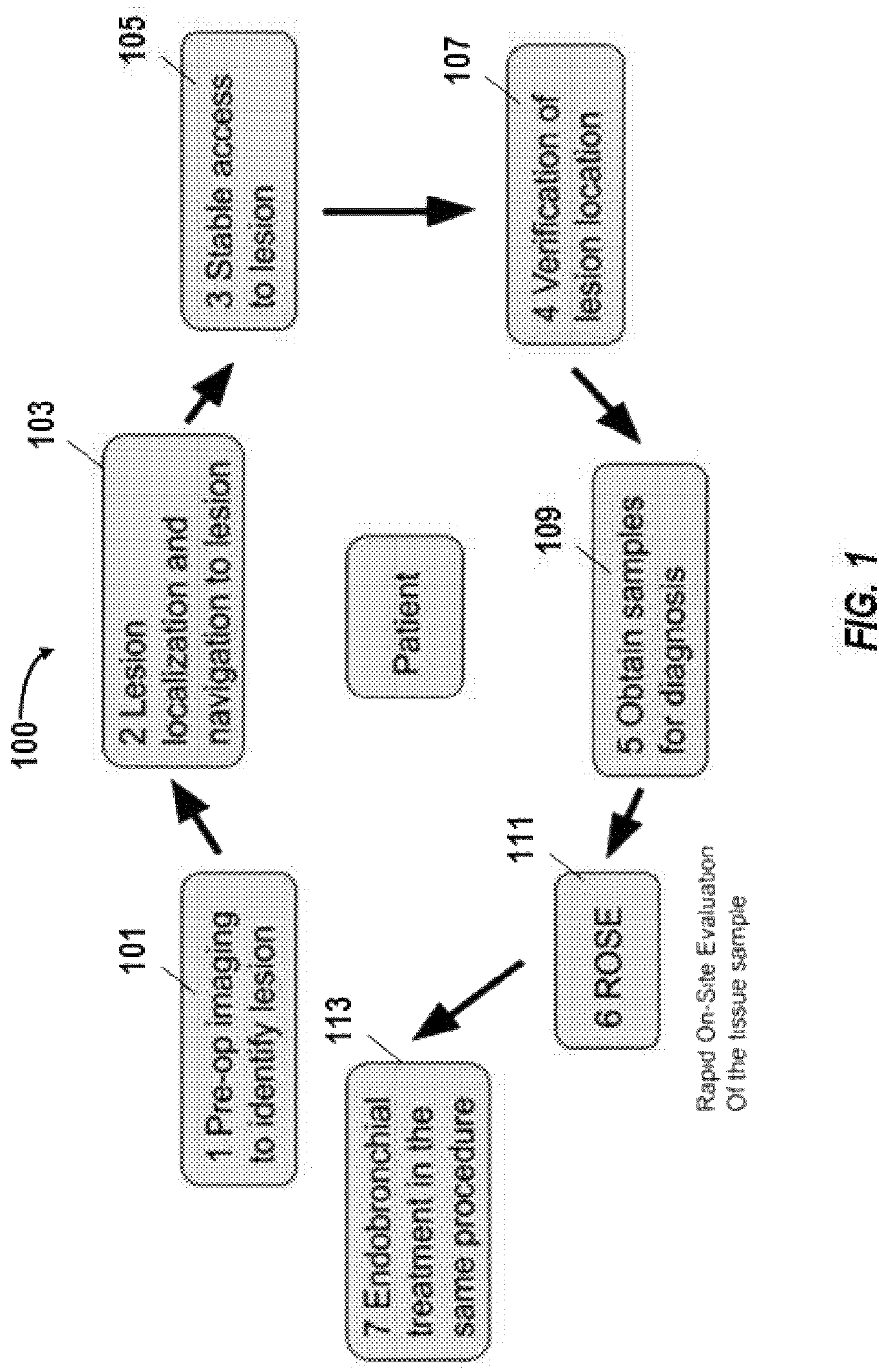
FIG. 1 shows an example workflow of lung cancer diagnosis enabled by the robotic bronchoscopy system described herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

While exemplary embodiments will be primarily directed at a bronchoscope, one of skill in the art will appreciate that this is not intended to be limiting, and the devices described herein may be used for other therapeutic or diagnostic procedures and in other anatomical regions of a patient's body such as a digestive system, including but not limited to the esophagus, liver, stomach, colon, urinary tract, or a respiratory system, including but not limited to the bronchus, the lung, and various others.

The embodiments disclosed herein can be combined in one or more of many ways to provide improved diagnosis and therapy to a patient. The disclosed embodiments can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Although the treatment planning and definition of diagnosis or surgical procedures as described herein are presented in the context of pulmonary diagnosis or surgery, the methods and apparatus as described herein can be used to treat any tissue of the body and any organ and vessel of the body such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein a processor encompasses one or more processors, for example a single processor, or a plurality of processors of a distributed processing system for example. A controller or processor as described herein generally comprises a tangible medium to store instructions to implement steps of a process, and the processor may comprise one or more of a central processing unit, programmable array logic, gate array logic, or a field programmable gate array, for example. In some cases, the one or more processors may be a programmable processor (e.g., a central processing unit (CPU) or a microcontroller), digital signal processors (DSPs), a field programmable gate array (FPGA) and/or one or more Advanced RISC Machine (ARM) processors. In some cases, the one or more processors may be operatively coupled to a non-transitory computer readable medium. The non-transitory computer readable medium can store logic, code, and/or program instructions executable by the one or more processors unit for performing one or more steps. The non-transitory computer readable medium can include one or more memory units (e.g., removable media or external storage such as an SD card or random access memory (RAM)). One or more methods or operations disclosed herein can be implemented in hardware components or combinations of hardware and software such as, for example, ASICs, special purpose computers, or general purpose computers.

As used herein, the terms distal and proximal may generally refer to locations referenced from the apparatus, and can be opposite of anatomical references. For example, a distal location of a bronchoscope or catheter may correspond to a proximal location of an elongate member of the patient, and a proximal location of the bronchoscope or catheter may correspond to a distal location of the elongate member of the patient.

A system as described herein, includes an elongate portion or elongate member such as a catheter. The terms "elongate member", "catheter", "bronchoscope" are used interchangeably throughout the specification unless contexts suggest otherwise. The elongate member can be placed directly into the body lumen or a body cavity. In some embodiments, the system may further include a support apparatus such as a robotic manipulator (e.g., robotic arm) to drive, support, position or control the movements and/or operation of the elongate member. Alternatively or in addition to, the support apparatus may be a hand-held device or other control devices that may or may not include a robotic system. In some embodiments, the system may further include peripheral devices and subsystems such as imaging systems that would assist and/or facilitate the navigation of the elongate member to the target site in the body of a subject. Such navigation may require a registration process which will be described later herein.

In some embodiments of the present disclosure, a robotic endoscopic (e.g., bronchoscopy) system is provided for performing surgical operations or diagnosis with improved performance at low cost. For example, the robotic bronchoscopy system may comprise a steerable catheter that can be entirely disposable. This may beneficially reduce the requirement of sterilization which can be high in cost or difficult to operate, yet the sterilization or sanitization may not be effective. Moreover, one challenge in bronchoscopy is reaching the upper lobe of the lung while navigating through the airways. In some cases, the provided robotic bronchoscopy system may be designed with capability to navigate through the airway having a small bending curvature in an autonomous or semi-autonomous manner. The autonomous or semi-autonomous navigation may require a registration process. Alternatively, the robotic bronchoscopy system may be navigated by an operator through a control system with vision guidance.

A typical lung cancer diagnosis and surgical treatment process can vary drastically, depending on the techniques used by healthcare providers, the clinical protocols, and the clinical sites. The inconsistent processes may cause delay to diagnose lung cancers in early stage, high cost of healthcare system and the patients to diagnose and treat lung cancers, and high risk of clinical and procedural complications. The provided robotic bronchoscopy system may allow for standardized early lung cancer diagnosis and treatment. FIG. 1 shows an example workflow 100 of standardized lung cancer diagnosis enabled by the robotic bronchoscopy system described herein.

As illustrated in FIG. 1, in some cases, a pre-operative imaging may be performed to identify lesions 101, and/or to identify the airways which will be used for registration and navigation during the procedure. Any suitable imaging modalities such as magnetic resonance (MR), positron emission tomography (PET), X-ray, computed tomography (CT) and ultrasound may be used to identify lesions or regions of interest. For instance, a patient with suspect lung cancer may be administered a pre-operative CT scan and suspect lung nodules may be identified in the CT images. The pre-operative imaging process can be performed prior to the bronchoscopy. The CT images may be analyzed to generate a map to guide the navigation of the robotic bronchoscope 103 at the time of bronchoscopy. For example, the lesion or the region of interest (ROI) may be segmented on the images. When the lung is under imaging, the passage or pathway to the lesion may be highlighted on the reconstructed images for planning a navigation path. The reconstructed images may guide the navigation of the robotic bronchoscope to the target tissue or target site. In some cases, the navigation path may be pre-planned using 3D image data. For instance, the catheter may be advanced toward the target site under a robotic control of the robotic bronchoscope system. The catheter may be steered or advanced towards the target site in a manual manner, an autonomous manner, or a semi-autonomous manner. In an example, the movement of the catheter may be image guided such that the insertion and/or steering direction may be controlled automatically. In some cases, the pre-operation image data may be used to generate a virtual model of the airway along with overlay of navigation path.

In some cases, the lesion location in the pre-operative imaging may not be accurate due to various reasons, such as CT to body divergence. In such cases, the lesion location may be verified 107 when the tip of the endoscope is near or within proximity of the target e.g., lesion 105. prior to a surgical procedure (e.g., biopsy or treatment). The accurate location of the lesion may be verified or updated with aid of the robotic bronchoscopy system. For instance, the bronchoscopy system may provide interface to imaging modalities such as real-time fluoroscopy to provide in vivo real-time imaging of the target site and the surrounding areas to locate the lesion. In an example, a C-arm or O-arm fluoroscopic imaging system may be used to generate a tomosynthesis or Cone Beam CT image for verifying or updating the location of the lesion 107.

Proceeding to the surgical procedures such as biopsy 109, various surgical tools such as biopsy tools, brushes or forceps may be inserted into the working channel of the catheter to perform biopsy or other surgical procedures manually or automatically. In some cases, another fluoroscopy (tomosynthesis) may be performed to confirm the tools have reached the target site, i.e., tool-in-lesion confirmation. The tool-in-lesion confirmation may be repeated on demand as further described with respect to FIG. 11. The present disclosure provides a navigation method with integrated tool-in-lesion detection based on digital tomosynthesis and the tomo reconstruction coordinate technique. Details about the method are described with respect to FIGS. 2-10.

In some cases, once the tool is confirmed to be within a target (e.g., lesion), samples of the lesion or any other target tissue may be obtained by the tools inserted through the working channel of the catheter 109. The system allows for camera visualization to be maintained throughout the procedure, including during the insertion of tools through the working channel. In some cases, the tissue sample may be rapidly evaluated on-site by a rapid on-site evaluation process to determine whether repetition of the tissue sampling is needed, or to decide further action 111. In some cases, the rapid on-site evaluation process may also provide a quick analysis on the tissue sample to determine the following surgical treatment. For instance, if the tissue sample is determined to be malignant as a result of the rapid on-site evaluation process, a manual or robotic treatment instrument may be inserted through the working channel of the robotic bronchoscope and perform endobronchial treatment of the lung cancer 113. This beneficially allows for diagnosis and treatment being performed in one session thereby providing targeted, painless, and fast treatment of early stage lung cancer.

As described above, once the catheter is navigated to the target region e.g., lesion, a tool such as a needle may be extended over the catheter and inserted into the target region. For example, after a biopsy needle is placed inside of a corrected target region e.g., lesion, it is desirable to confirm whether the tool is truly within the legion. In some cases, fluoroscopic image may be acquired after the tip of catheter reached the target site to confirm the location of the catheter with respect to the target location in real-time. In some embodiments, the present disclosure provides methods and systems for providing the tool-in-lesion confirmation in a quantitative manner. The tool-in-lesion confirmation method may comprise a tomosynthesis-based method which will be described later herein. In some cases, once the final position is confirmed, cone beam CT scan may be captured (e.g., 8 second sweep, 0.5 projection/degree, 396 projections) and used to perform a CBCT tool-in-lesion confirmation.

In some cases, tool-in-lesion confirmation may be defined as a thin tool (e.g., needle) placement either in or tangential to the lesion in three orthogonal planes (axial, sagittal and coronal). Alternatively, tool-in-lesion may not include the tangential situation. FIG. 2 schematically illustrates examples of tool-in-lesion 200 and examples of not tool-in-lesion 210. As shown in the examples, tool-in-lesion may be defined as a tool, e.g., biopsy needle, in or tangential to the lesion. It should be noted that although the method herein is described with respect to determining a biopsy needle in lesion, the method is not limited to the types, shapes or dimension of tool, or the types, shape or dimension of target region. For example, the tools can be any tool other than needle and the target region may or may not be lesion. The tool-in-lesion confirmation method can be applied to any situations where a relative position of a tool with respect to a target region is needed.

In an aspect of the present disclosure, a method for real-time tool-in-lesion confirmation is provided. In some embodiments, the method may be tomosynthesis-based method. As described above, tomosynthesis reconstruction does not have uniform resolution. The sweep angle and number of projections determines resolution. Tomosynthesis imaging data in the Fourier domain are incomplete owing to the limited sweep angle and small number of projections, and creating accurate tomosynthesis image reconstructions is challenging. The nonisotropic geometry degrades z-axis (i.e., depth direction) image resolution, which is derived from the Fourier domain rather than directly acquired. The z-axis resolution is improved by increasing the range of the sweep angle. However, given dose constraints, there is an optimal number of projections for a certain sweep-angle range beyond which the in-plane (i.e., x, y axis) image quality decreases with the number of projections without any further improvement of the z-axis resolution. The term "depth direction" as utilized herein may refer to the vertical direction or direction of the central ray. A slice stacked in the depth direction may be an in-plane slice.

In some cases, reconstructed 3D volume images are viewed as multiple thin (e.g., 0.5-1 mm) slices parallel to the detector plane. Unlike CT, tomosynthesis slice thickness and reconstruction intervals do not have a one-to-one correspondence with the compression thickness. The standard way to show a 3D volume dataset by three orthogonal planes (e.g., axial, sagittal and coronal) is ineffective since two of the planes have poorer resolution. When a stack of 2D reconstructed image slices are presented on the display screen, a user may view each image slice in the coronal plane and go through the stack of slices in the anterior-posterior (AP) direction. The image stack is typically oriented parallel to the detector plane with each image separated by a predetermined depth (e.g., 1 mm).

In some embodiments, the system provides real time intraoperative imaging to confirm tool-in-lesion and to overcome CT-to-body divergence. The digital tomosynthesis tool in lesion confirmation may involve a tomosynthesis reconstruction Coordinate Technique. In some cases, the reconstructed tomosynthesis image is displayed in a user interface with quantitative tool-in-lesion information. In some cases, the quantitative tool-in-lesion information may be based on a coordinate that represents the depth of the displayed slice within the reconstruction in the anterior-posterior (AP) direction. Details about reconstruction of tomosynthesis image are described later herein.

Figure 3:
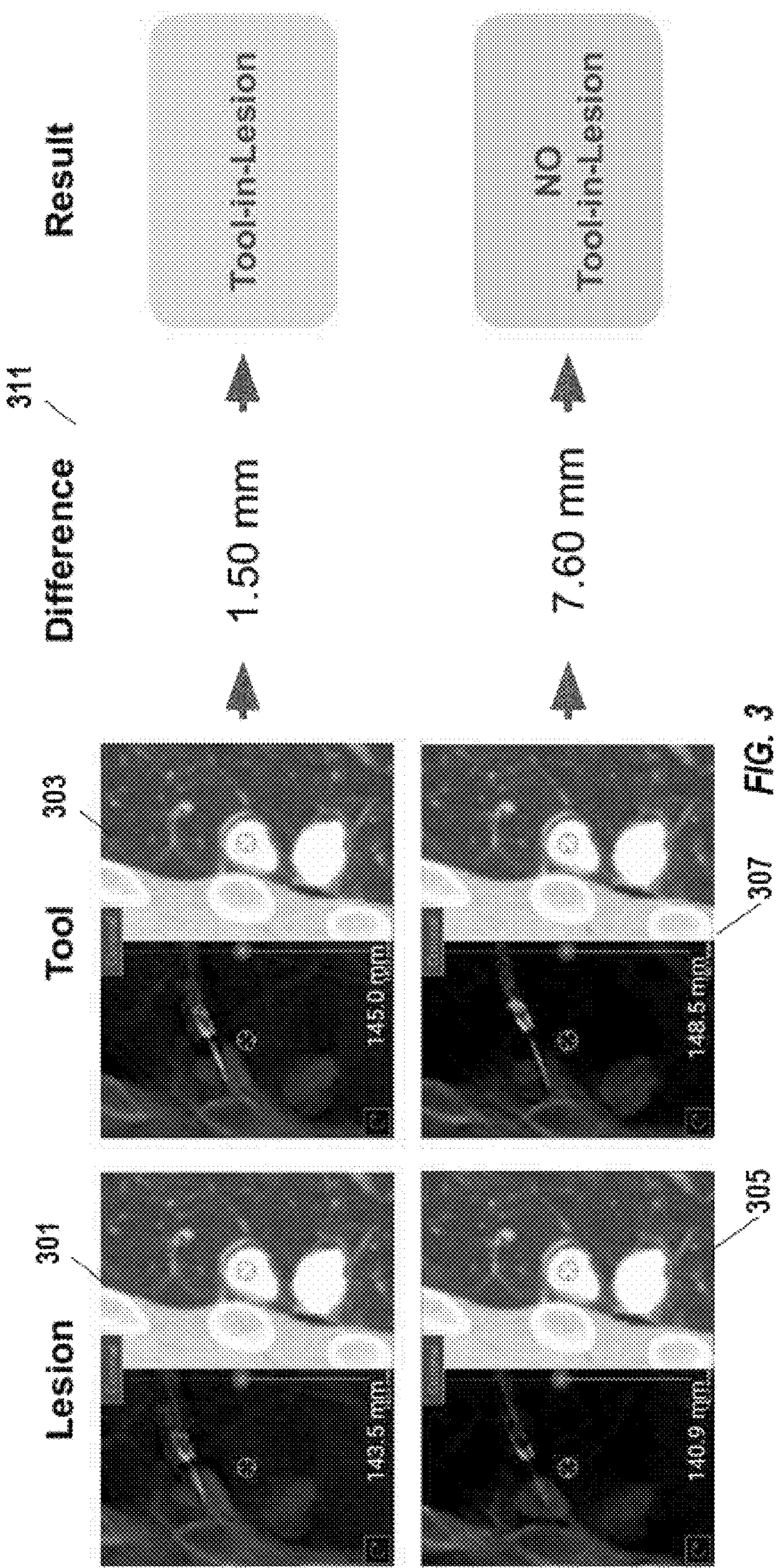
FIG. 3 shows an example of a graphical user interface (GUI) showing the reconstructed tomosynthesis image with quantitative tool-in-lesion information.

FIG. 3 shows an example of a graphical user interface (GUI) displaying the reconstructed tomosynthesis image with quantitative tool-in-lesion information. The tomosynthesis image may be constructed using any suitable reconstruction algorithm (e.g., filter backprojection (FBP), iterative algorithm such as algebraic reconstruction technique (ART), etc.) to the multiple projections, yielding a 3-D volume dataset. As shown in the example, the coordinate, e.g., depth of the displayed slice in the AP direction is displayed along with the image.

Figure 4:
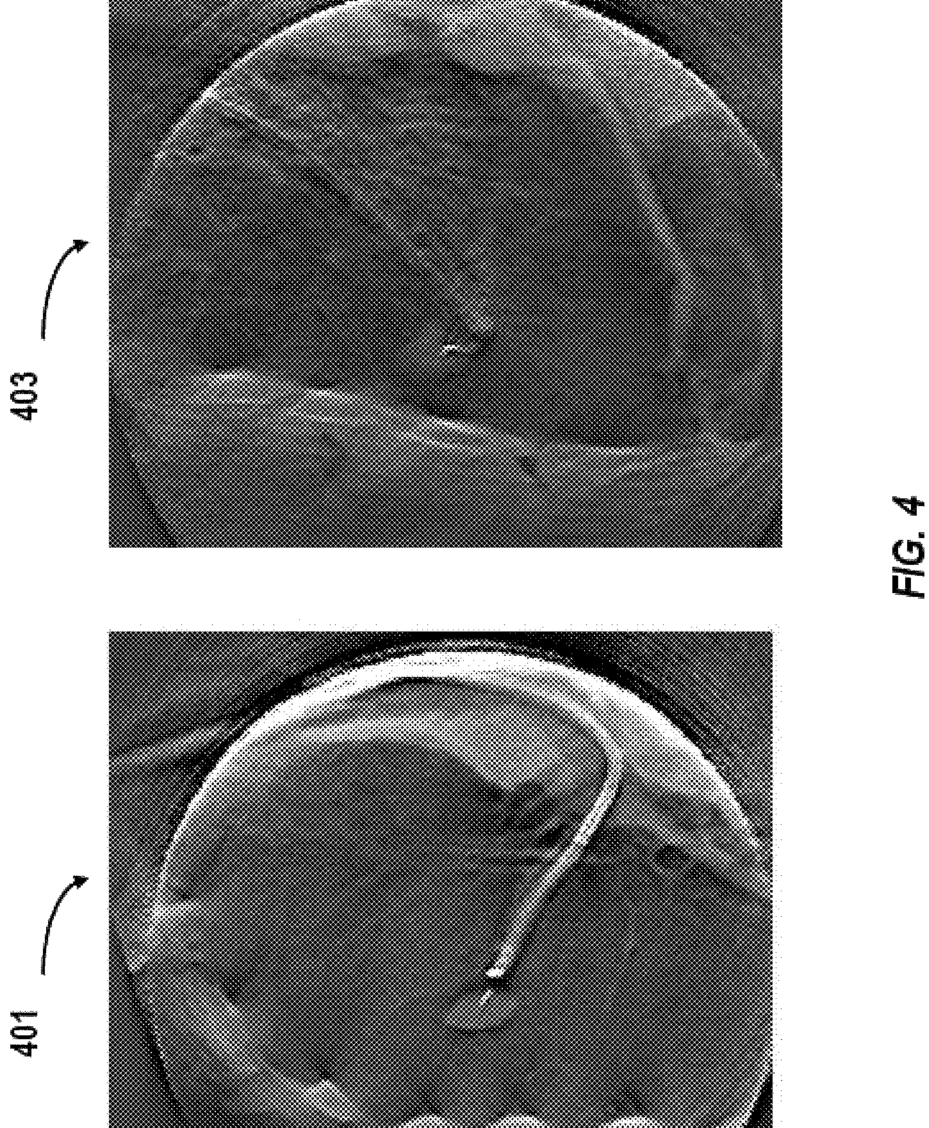
FIG. 4 shows examples of optimal slices of the tool.

In the first example, the coordinate of the slice of the lesion 301 (e.g., 143.5 mm) and the coordinate of the slice of the tool 303 (e.g., 145.0 mm) is determined and displayed on the screen. In some cases, the slice of the lesion 301, 305 may be an optimal image slice of the lesion that is in focus. This may be determined based on sharpness or contrast metric of the slice. In some cases, the slice of the tool 303, 307 may be an optimal image of the tool that is in focus. This may also be determined based on the sharpness or contrast of the image slice. FIG. 4 shows examples of optimal slices of the tool. The optimal slice for the tool (e.g. tip of needle) may be the slice showing the entire needle 401 in focus or a slice 403 showing a section of the needle that are within the lesion area that is in focus.

In some embodiments, the coordinate information is used to determine whether the tool is in the lesion by calculating the difference between the coordinates for the depths of optimal slices for needle and the lesion respectively. Referring back to FIG. 3, the distance 311 between the optimal image slice of the needle 301, 305 and the optimal image of the lesion 305, 507 may then be calculated and used to determine whether the needle is within the lesion. The distance 311 may be the depth difference (e.g., coordinates in the depth/AP direction) between the slice with the tool in focus and the slice with the lesion in focus.

In some embodiments, the method may comprise comparing the distance 311 to a threshold to determine whether the tool is in the lesion. In some cases, the threshold may be determined based on the nodule size (or lesion size) that is determined by the average of the longest and shortest dimensions on the pre-planning CT scan of the subject (patient). For example, if the average of the longest and shortest dimensions of the target lesion on the pre-planning CT scan is 4 mm, the depth difference between the optimal image of the lesion 301 and the optimal image of the needle 303 is 1.5 mm which is below the 4 mm threshold, the GUI may display the result as tool-in-lesion. In the other example, the distance is 7.6 mm which is above the threshold, then the GUI may display the result as no tool-in-lesion.

The threshold for determining tool-in-lesion can be generated using various methods. In some embodiments, the threshold may be determined based at least in part on the dimension of the lesion in the same subject. In some cases, the threshold may be the average of the longest and shortest dimensions on the pre-planning CT scan of the subject. In some cases, the threshold may be the radius of the lesion in the AP direction which is obtained from the pre-planning scan of the subject or any scan performed during the operation (e.g., 3D scan performed during navigation or when the endoscope is near the target). In some cases, the threshold may include a margin such that if $abs(x-y)<r-e$ (where r is the radius of the lesion in the AP direction, e is a margin, x, y are the depth coordinates of the optimal tool slice and optimal lesion slice), the tool is within the lesion, else if $abs(x-y)>r+e$ the tool is not in the lesion, otherwise the tool is on the border/tangential if $abs(x-y)=r+e$. In some cases, the margin e may be determined based on empirical data. For example, empirical data, physician provided data, or historical data on a size of similar lesion may be utilized to determine the margin.

The optimal slice of the tool and/or the optimal slice of the lesion can be determined using various suitable methods. In some embodiments, the optimal slice of the lesion can be selected via the GUI by the user visually identifying a slice with the lesion in focus. For instance, a user may scroll through slices in the depth direction and may mark a slice as the optimal slice that the lesion or needle has the sharpest edge or best contrast, Alternatively, the optimal slice of the lesion and/or the tool may be determined automatically. For instance, the software may perform automatic focus analysis of the stack of images, such as by defining a sharpness or contrast metric and select the slice which maximizes the chosen metric. For example, sharpness and/or contrast of the lesion region in each slice may be calculated and the slice with the maximum sharpness measurement may be automatically determined to be the optimal slice for the lesion.

Figure 5:
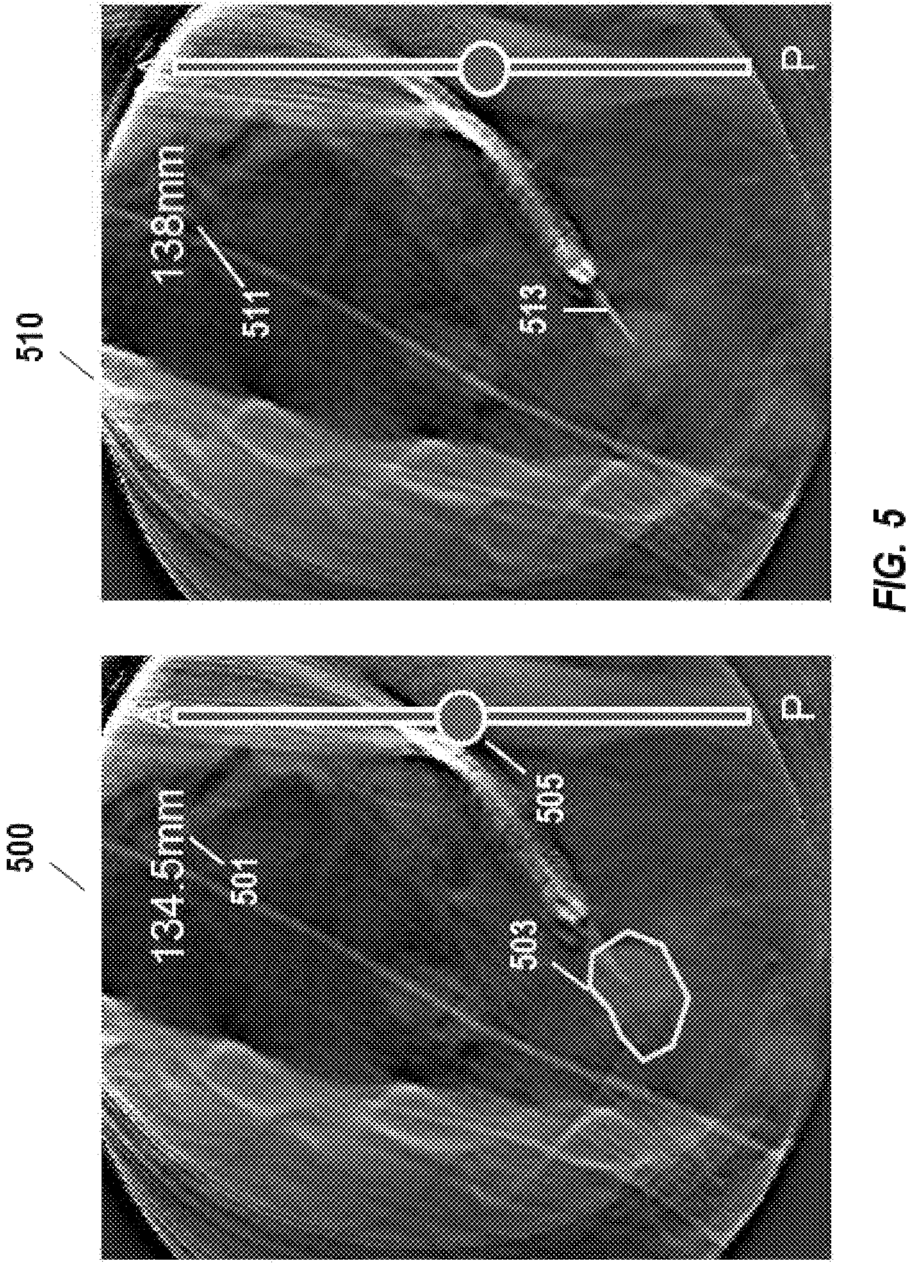
FIGS. 5-9 show various examples of GUI for assisting the tool-in-lesion confirmation.

In some embodiments, the GUI herein may provide visual indicators or interactive visual guidance for a user to interact with the image slices and assist in the tool-in-lesion determination. FIGS. 5-9 show various examples of GUI for assisting the tool-in-lesion confirmation. FIG. 5 shows an example of GUI for the tool-in-lesion detection. The GUI may display tomosynthesis volume image with an interactive graphical element (e.g., sliding bar) 505 allowing a user to scroll through the stack of slices in the AP direction (depth direction). As shown in the example, a depth coordinate 501, 511 associated with a currently displayed slice may also be displayed such as by overlaying the coordinates on the image slice. A user may slide the bar to scroll through the slices. The user may identify a first slice 500 when a lesion 503 is in focus and obtain the associated depth coordinate 501. For example, the user may click on the slice and mark it as optimal slice then the associated depth coordinate is automatically recorded by the system. In some cases, the coordinate of the first slice may be identified as the center of the lesion in the AP direction. The user may then identify a second slice 510 when the tool 513 is in focus and obtain the associated depth coordinate 511. Next, the coordinate difference between the second slice and center of the lesion in the AP direction is calculated (e.g., abs (138 mm-134.5 mm)) and compared against a threshold to determine whether the tool is within the lesion.

Figure 6:
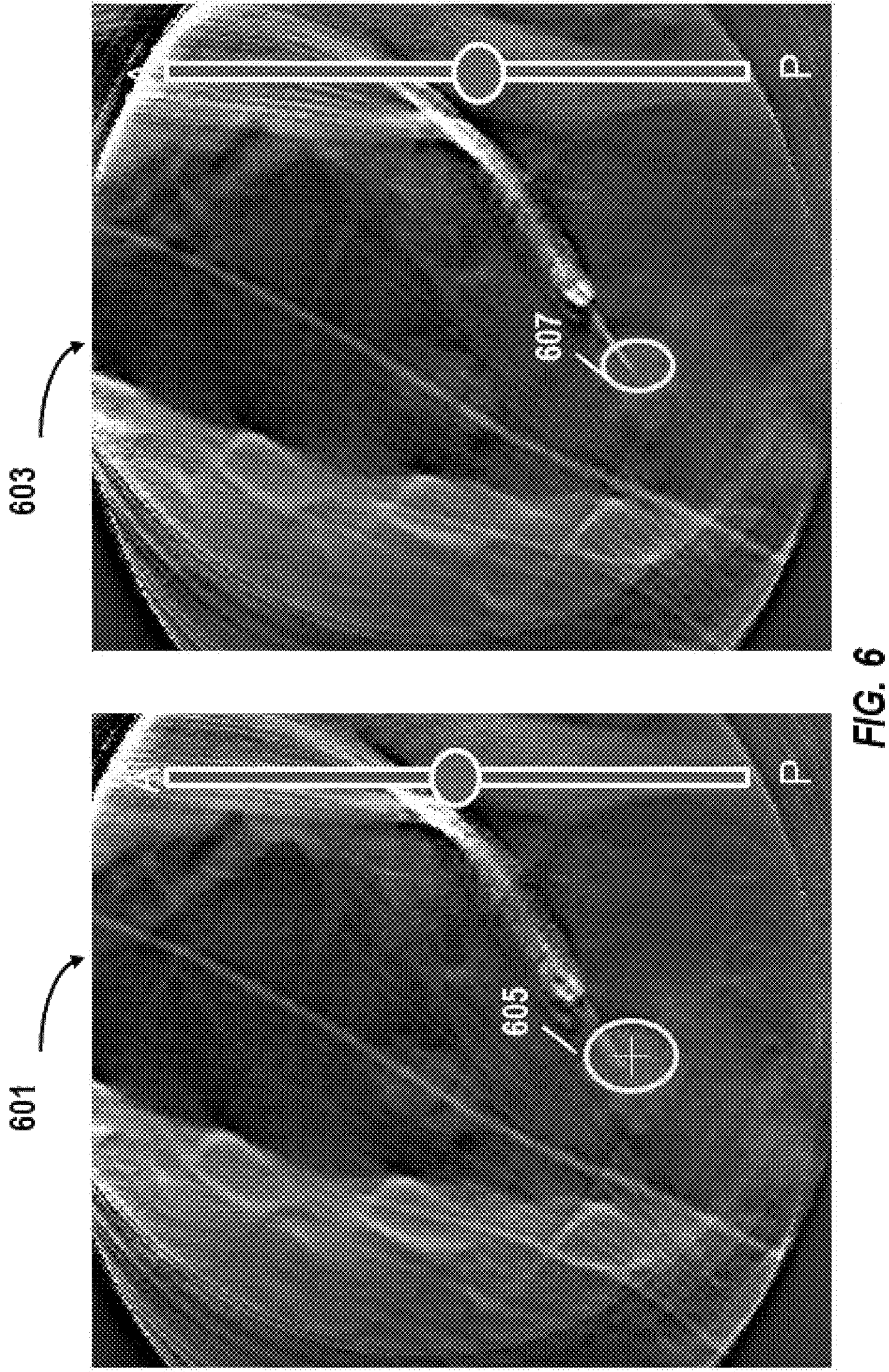

In some cases, a mask, outline or contour of the lesion in each slice may be overlaid on top of the tomosynthesis image to assist in the tool-in-lesion confirmation. FIG. 6 shows an example of a GUI displaying an outline or boundary of the lesion in each slice. A user may scroll through the stack of slices and identify a first slice with the lesion in focus (e.g., lesion boundary has the best sharpness), and may provide an input via the GUI indicating the coordinate of the first slice is the center of the lesion. For example, the user may click on the first slice 601 to select it as the optimal slice of lesion. Based on the center coordinate of the lesion, the system may automatically register a 3D model of the lesion to the image and determine an intersection between the 3D lesion model and each of the slices. The 3D lesion model may be obtained from previous scan of the subject such as from the CT pre-planning process. For example, the pre-operation image may be used to create a virtual model of the target tissue by segmenting the target lesion from the image data. The intersection may be used to generate a mask or contour of the lesion 605, 607 in each slice and is overlaid onto the image slice. The user may then scroll through the slices and identify a second slice 603 when the tool (e.g., biopsy needle) is focus or at least a part of the tool is in focus. The user may determine the tool is in lesion when the mask or contour of the lesion 607 appears within the second slice. In another example, if the mast or contour does not appear in the second slice where the tool is in focus, it may indicate that the tool is not in the lesion. Such visual indicator beneficially helps a user to confirm tool-in-lesion in an intuitive manner.

Figure 7:
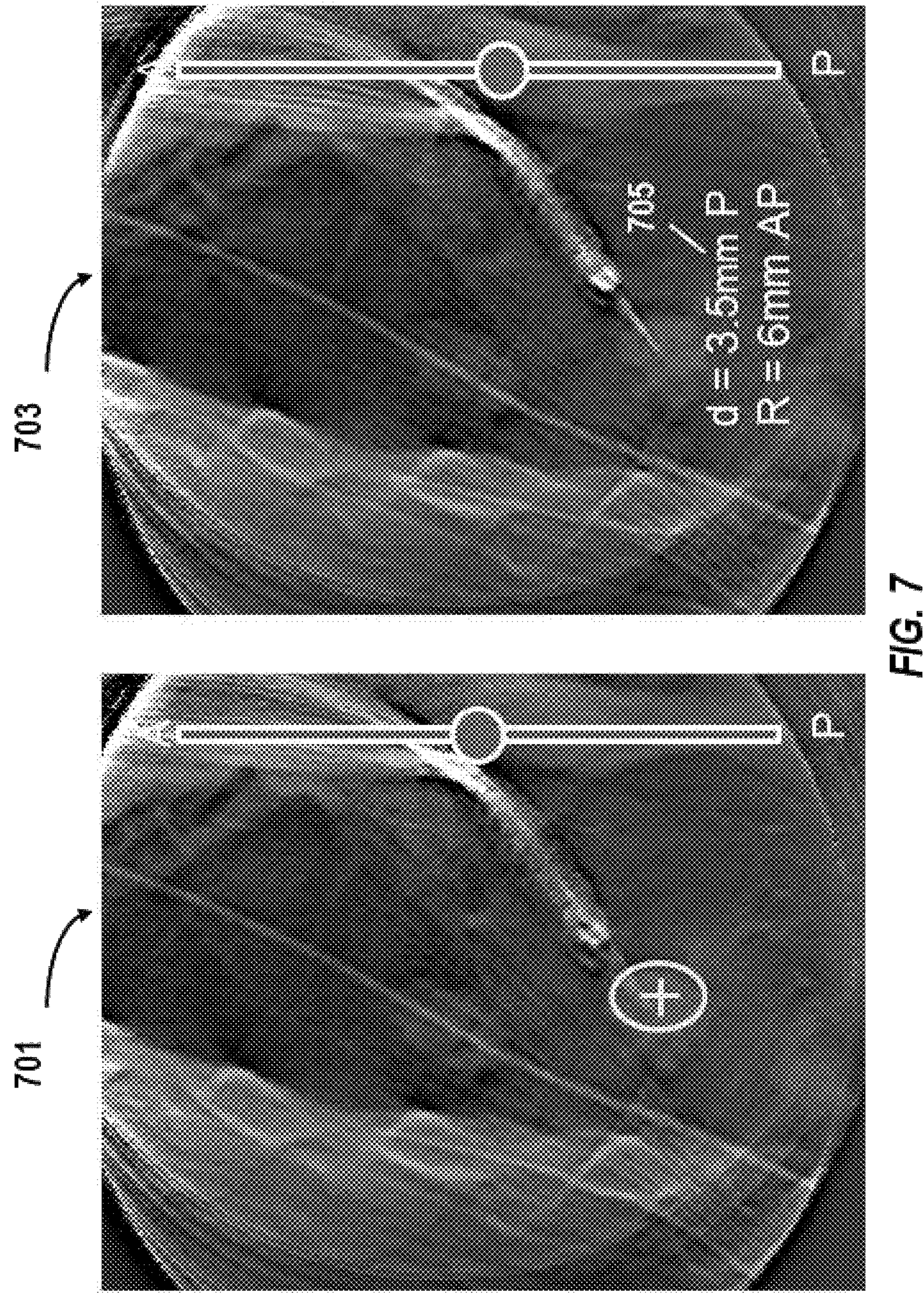

In some cases, instead of displaying an intersection/cross-section of the lesion in each slice, a radius of the lesion in the AP direction may be displayed as a reference. FIG. 7 shows another example of a GUI. In the example, once a user identifies a slice of the lesion in focus 701 (e.g., best sharpness of the contour or best contrast), the coordinate of the slice may be used as a center of the lesion. Next, a radius of the lesion in the AP direction (e.g., R=6 mm AP) and a distance between a current slice 703 and the center of the lesion may be displayed 705 (e.g., d=3.5 mm) in each slice. The user may find the second slice with the tool in focus and examine whether the corresponding distance d of the second slice is greater than the radius R. If so, it indicates the tool is not in the lesion.

Figure 8:
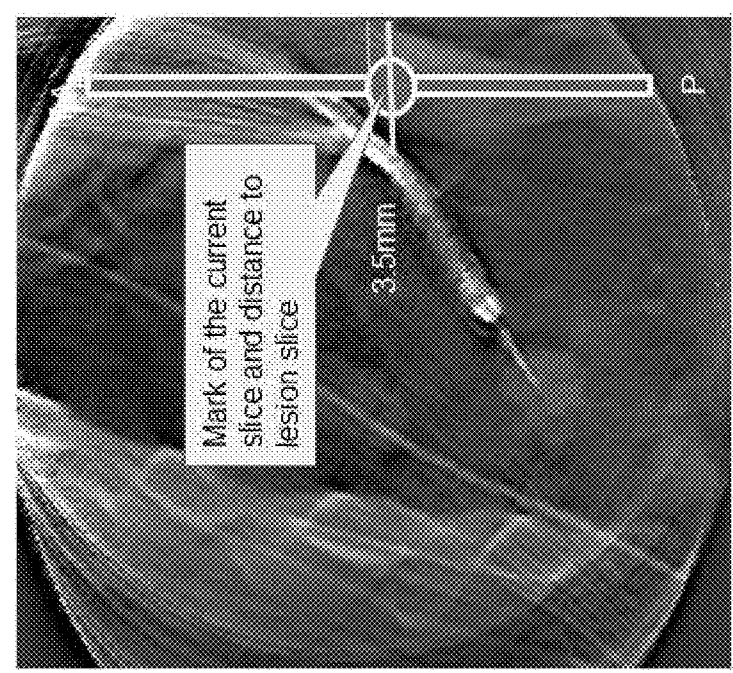
Figure 8:
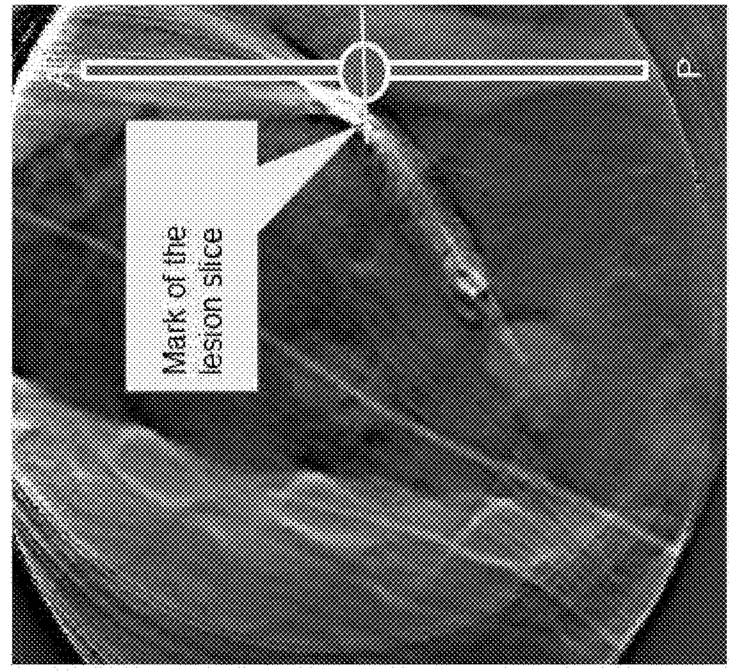
Figure 9:
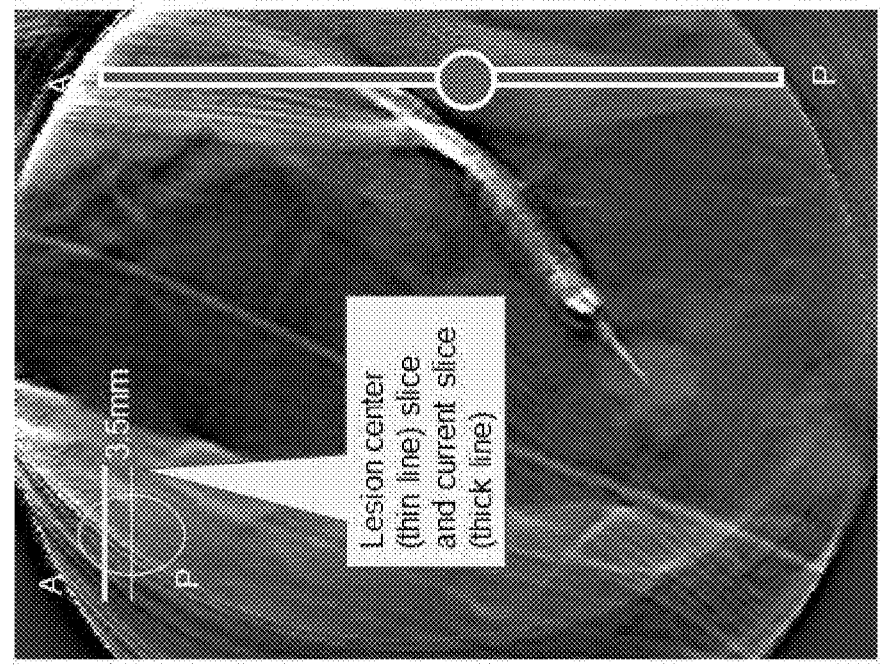
Figure 9:
Figure 9:
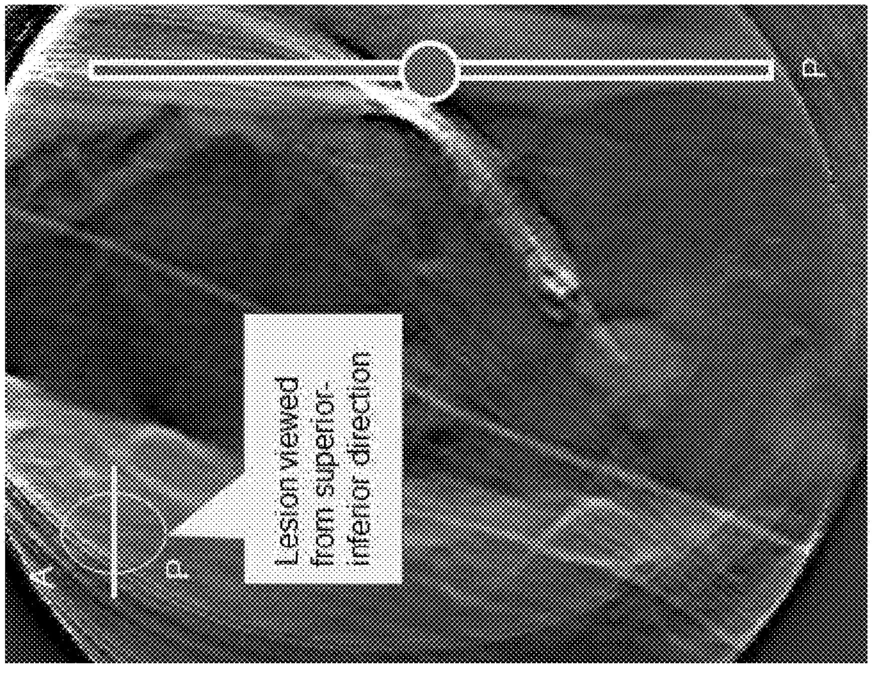

FIGS. 8 and 9 show examples of GUIs displaying depth difference between the slice of the lesion and the slice of tool. In the illustrated example, once a user identifies a slice of the lesion in focus, i.e., optimal slice for the lesion, the user may provide an input via the GUI such as by right clicking on the image to mark the current slice as the center of the lesion. A visual indicator representing the lesion center slice (e.g., a horizontal thick line) and an indicator representing the current slice (e.g., a horizontal thin line) may be displayed along with a distance between the two slices. The distance and the indicator of the current slice may be dynamically rendered along with the user scrolling through the slices.

In some embodiments, the optimal slice of the lesion (i.e., lesion is in most focus) or the optimal slice of the tool (i.e., tip of the tool, part of the tool, entire tool in most focus) may be determined by the software automatically. For example, a sharpness or contrast metric may be computed for each slice and the slice which maximizes the chosen metric may be selected. In some cases, the auto-selected slice may be suggested to the user within the GUI and the user may confirm the auto-selected slice or choose a different slice to represent the lesion center and/or the tool slice.\

Figure 19:
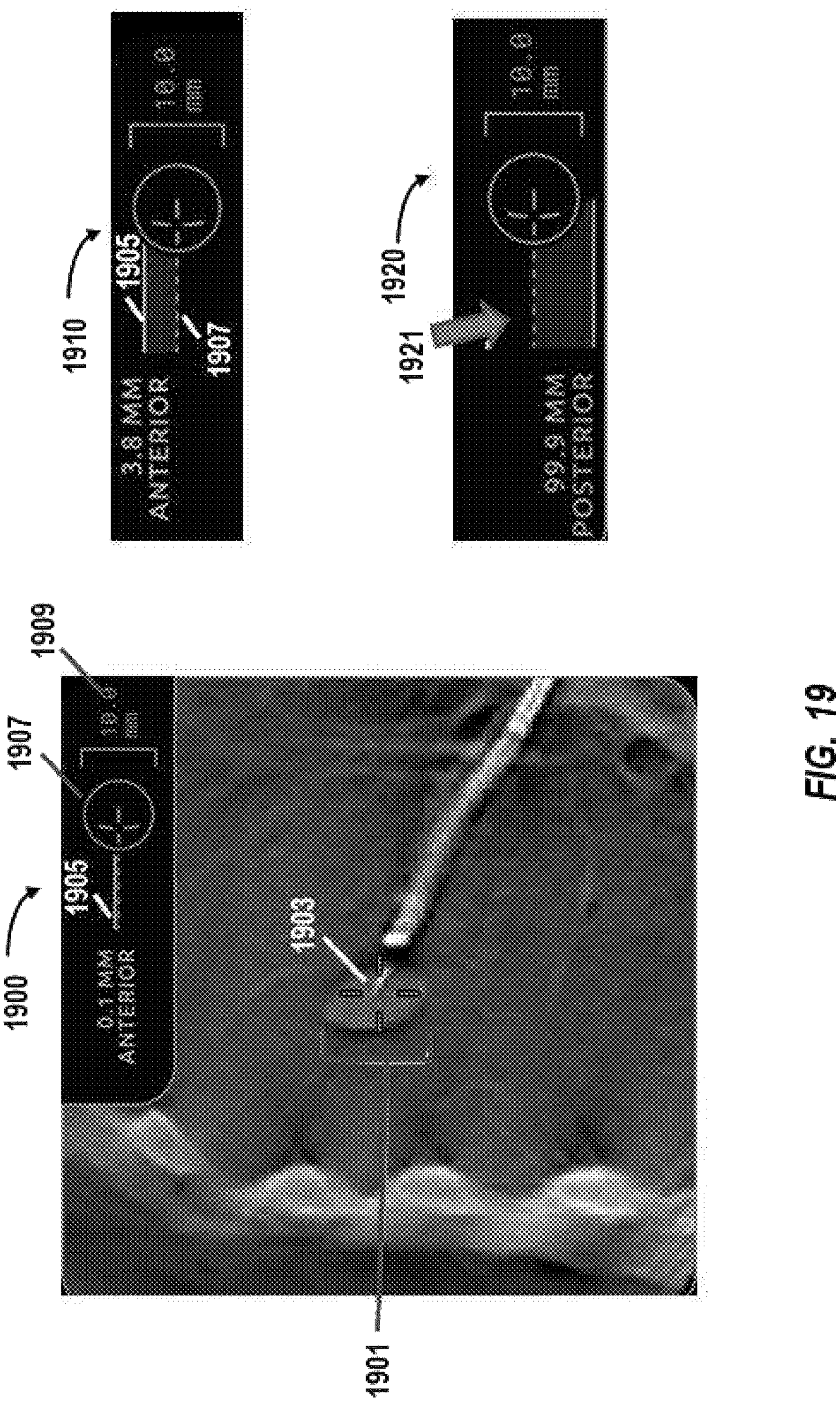
FIG. 19 and FIG. 20 show other examples of GUI displaying quantitative tool-in-lesion information.
Figure 20:
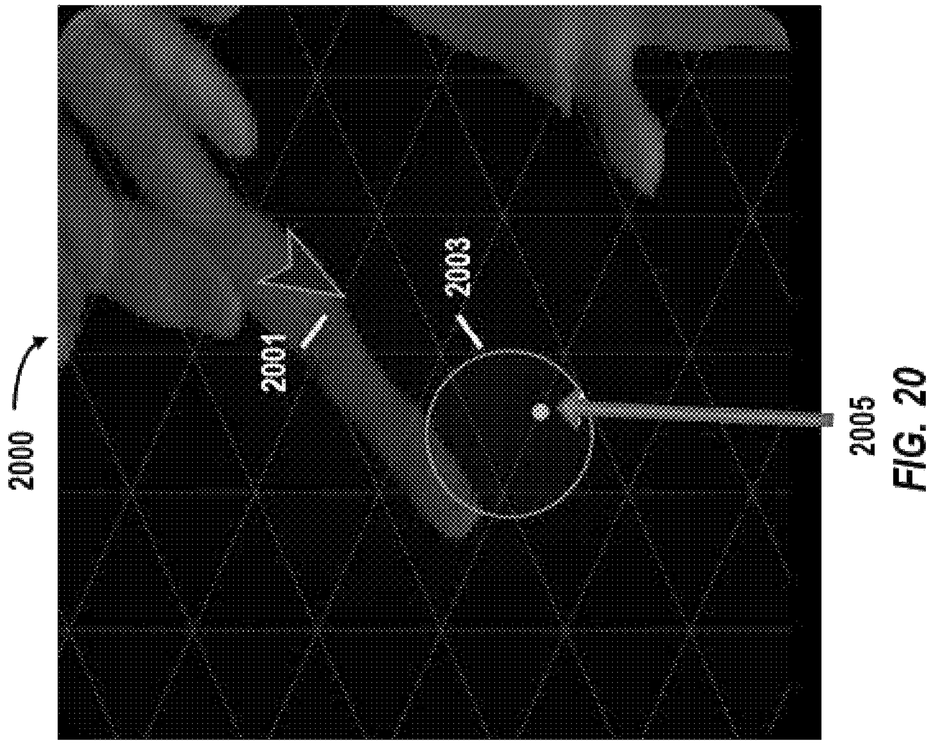

FIG. 19 and FIG. 20 show other examples 1900, 2000 of GUI displaying quantitative tool-in-lesion information. As shown in FIG. 19, an overlay of the lesion 1901 may be displayed on a slice. The overlay of lesion 1901 may be generated based on a 3D model of the lesion and intersection with the slice as described above. The overlay of lesion can bet toggled on and off by a user. A user may scroll through the slices and select the slice that the lesion is in best focus as the optimal slice. The depth of the optimal slice may then be automatically recorded as the center of the lesion in the depth direction. The user may then scroll through the slices and select the slice that needle tip is in best focus as the optimal slice for the needle. In some cases, as the user scrolls through the slices, quantitative information indicating the spatial relationship between the tool in the current slice and the lesion center may be dynamically displayed on the GUI. For example, the dashed line 1907 may represent depth location of the lesion center and the solid line 1905 may represent the depth location of the current slice of the needle. The distance between the needle (in the current slice or optimal slice) and the lesion center may be displayed (e.g., 0.1 mm anterior, 3.8 mm anterior, etc.). The GUI may further display the AP diameter of the target object or lesion 1909 (e.g., 10.0 mm) and display the target viewed from the right left direction 1907. In some cases, in addition to the quantitative indicator, color coding may be utilized to indicate whether the tool is in the lesion or outside of lesion. For example, when the tool is within the lesion such as shown in the examples 1900, 1910, the lines 1905, 1907 may be displayed in green, whereas when the tool is outside of the lesion such as shown in the example 1920, the line 1921 representing the tool optimal slice may be displayed in red color. FIG. 20 shows an example of GUI 2000 displaying a virtual view of the target (e.g., lesion) and tip of tool. As shown in the example 2000, a graphical visual indicator 2005 may be displayed on the virtual view representing location of the needle tip in 3D space. A second graphical indicator 2003 may be displayed representing the target or lesion in the 3D space. A third indicator 2001 may be displayed representing the tip of endoscope. The virtual view may be created based on pre-operation image data and/or later acquired 3D image data. The virtual view 2000 overlaid with the needle tip location, lesion location and the tip of the endoscope may beneficially allow a user to visualize the spatial relationship among the three objects.

Figure 10:
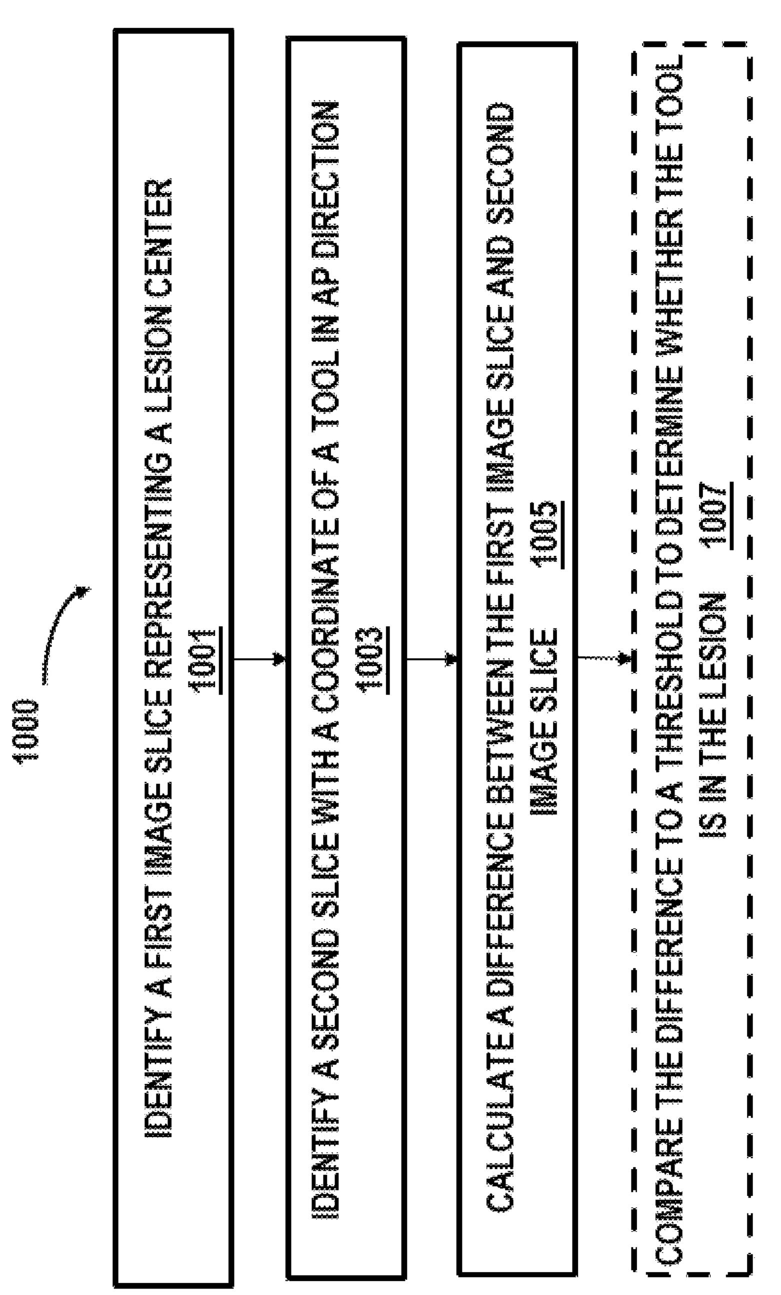
FIG. 10 shows an example of the tool-in-lesion algorithm, in accordance with some embodiments of the present disclosure.

FIG. 10 shows an example of the tool-in-lesion algorithm 1000, in accordance with some embodiments of the present disclosure. The method may comprise identifying a first image slice (e.g., tomosynthesis slice) representing a center of a target such as a lesion center 1001. The first image slice may be identified by a user within a GUI as described above. For example, a user may identify a slice that the lesion is in focus based on the sharpness and/or contrast of the slice. Alternatively or additionally, the first slice may be identified automatically based on the sharpness and contrast metric computed for each slice. For example, the algorithm may calculate the sharpness and/or contrast in the lesion region (e.g., a user drawing a box or region in the image slice indicating the likely location of the lesion) for each slice and the slice with the maximum metric value may be selected as the first slice. The coordinate of the first slice in the AP/depth direction may be used to mark the depth coordinate of the lesion center.

Next, a second image slice (e.g., tomosynthesis slice) corresponding to a tool in optimal focus may be identified 1003. The second slice may also be manually selected by a user via the GUI or automatically by the system by calculating the image metric such as sharpness or contrast. A difference between the coordinate of the first and second image slice in the AP/depth direction may be calculated 1005 and used to determine whether the tool is in the lesion. In some cases, the difference may be compared automatically against a threshold 1007. If the difference is equal to or below the threshold, the algorithm may output a result confirming the tool is in the lesion. Alternatively, if the difference is above the threshold, the algorithm may output a result indicating the tool is not in the lesion. The threshold can be determined using any suitable method as described above. For example, the threshold may be the average of the longest and shortest dimensions on the pre-planning CT scan of the subject. Alternatively, threshold may be the radius of the lesion in the AP direction which is obtained from the pre-planning scan of the subject or any scan performed during the operation. In some cases, the threshold may include a margin such that if $abs(x-y)<r-e$ (where r is the radius of the lesion in the AP direction, e is a margin, x, y are the depth coordinates of the optimal tool slice and optimal lesion slice), the tool is within the lesion, elseif $abs(x-y)>r+e$ the tool is not in the lesion, the tool is on the border if $abs(x-y)=r+e$. In some cases, the margin e may be determined based on empirical data.

Optionally, the algorithm may generate a visual indicator of the lesion intersecting each image slice (e.g., mask or contour of the lesion) based on a 3D lesion model and the lesion center coordinate determined in step 1001. A user may determine whether tool in the lesion by viewing the visual indicator overlaid on the second slice (when the tool is in focus).

Figure 11:
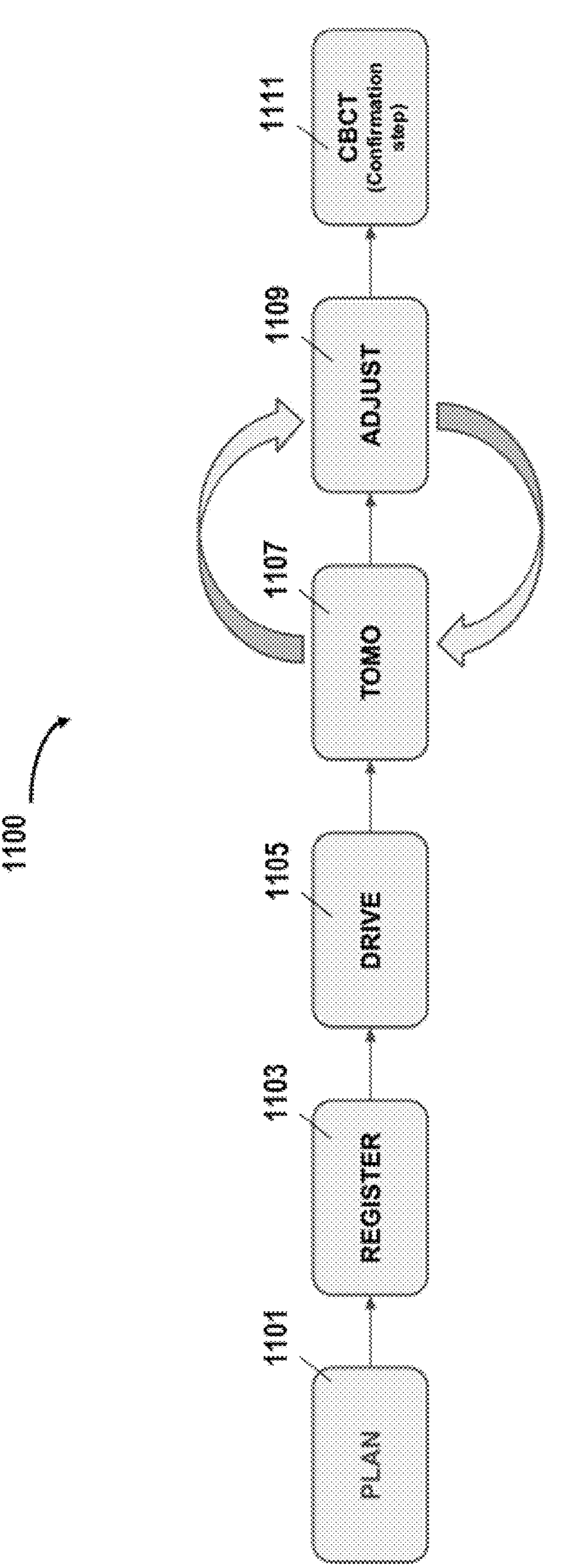
FIG. 11 shows an exemplary workflow of integrating tool-in-lesion determination into the robotic bronchoscopy system navigation.

FIG. 11 shows an exemplary workflow of integrating tool-in-lesion determination into the robotic bronchoscopy system navigation. As shown in the example, a planning software may be used to identify and segment target lesions as well as plan pathways. The robotic platform may be set up before an airway registration is performed, and an individual target lesion is selected. The catheter system may be guided to the desired target lesion using geopositional guidance. Next, a Tool in Lesion Tomo technology with augmented fluoroscopy (TILT+) sweep is performed utilizing a 2D fluoroscopic c-arm. In the example, the c-arm sweep comprises a limited angle circular rotation from 30 degrees left anterior oblique to 30 degrees right anterior oblique. The bronchoscope tip position is marked. Based on the reconstruction algorithm, two-dimensional images are stacked to create a section image. The target position is also marked on the section image. Details about reconstructing the 3D volume tomosynthesis image are described with respect to FIG. 13 and FIG. 21.

The catheter is then navigated to the corrected target and a needle is placed. If desired, the operator may utilize augmented fluoroscopy to help optimize bronchoscope and tool position. A repeat TILT sweep is performed to confirm tool in lesion confirmation. Repeated attempts can be allowed at the user's discretion until the needle is optimally positioned. Digital tomosynthesis tool in lesion confirmation is based on the TOMO reconstruction Coordinate Technique as described above.

Once the final position was confirmed, cone beam CT scan may be captured. The CBCT tool-in-lesion confirmation may be defined as needle placement either in or tangential to the lesion in three orthogonal planes (axial, sagittal and coronal).

Figure 12:
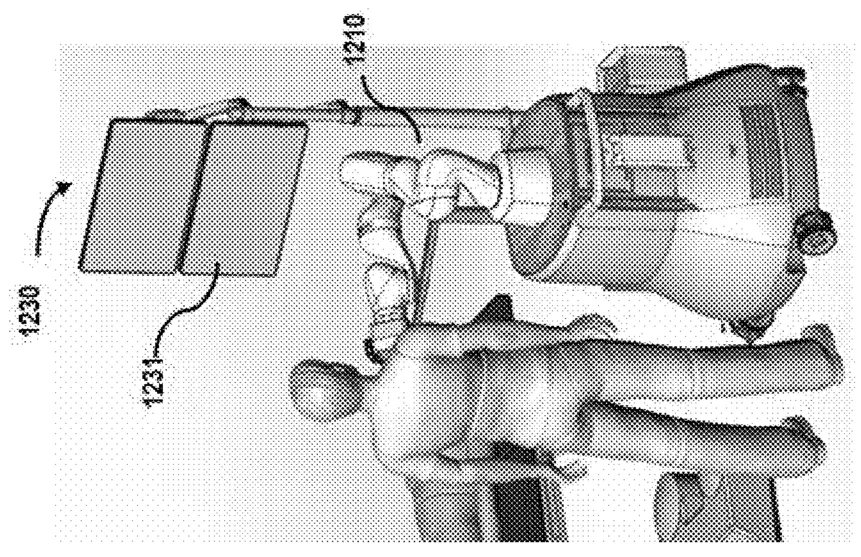
FIG. 12 shows examples of robotic bronchoscopy systems, in accordance with some embodiments of the invention.
Figure 12:
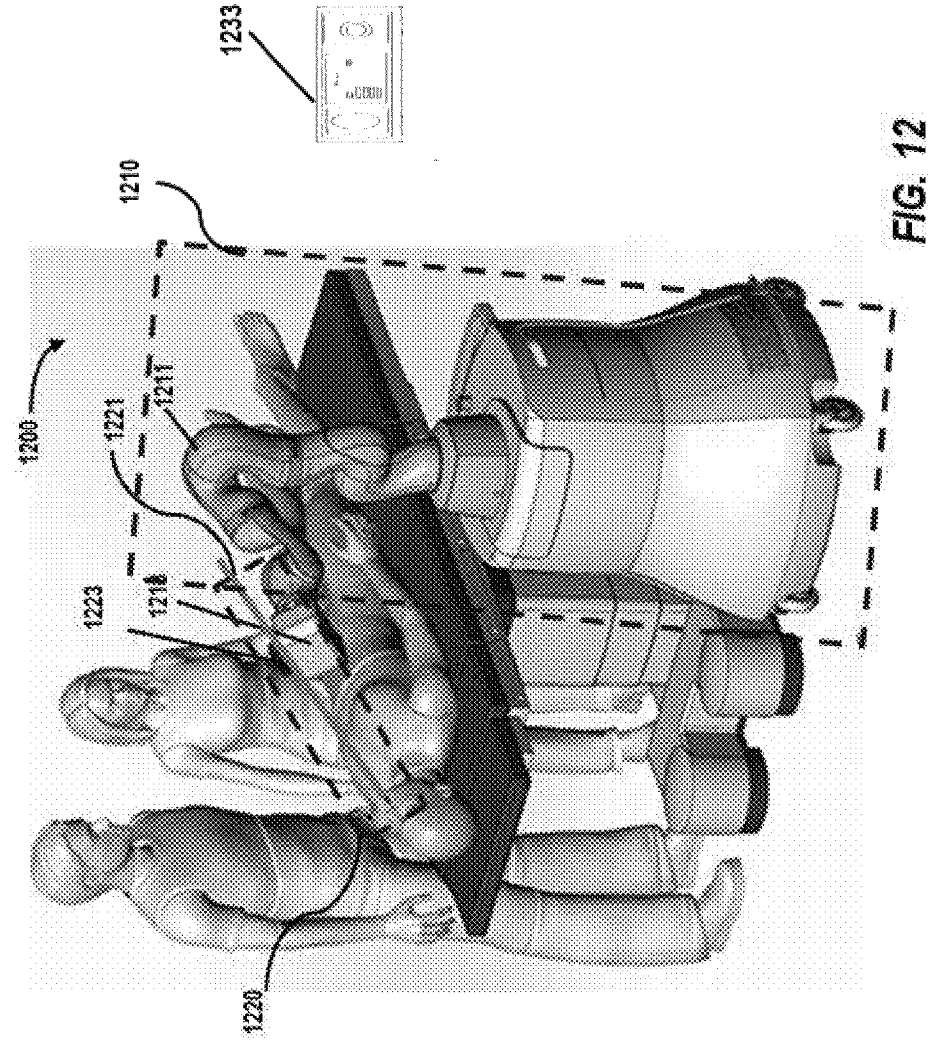

FIG. 12 show examples of robotic bronchoscopy system 1200, 1230, in accordance with some embodiments of the invention. As shown in FIG. 12, the robotic bronchoscopy system 1200 may comprise a steerable catheter assembly 1220 and a robotic support system 1210, for supporting or carrying the steerable catheter assembly. The steerable catheter assembly can be a bronchoscope. In some embodiments, the steerable catheter assembly may be a single-use robotic bronchoscope. In some embodiments, the robotic bronchoscopy system 1200 may comprise an instrument driving mechanism 1213 that is attached to the arm of the robotic support system. The instrument driving mechanism may be provided by any suitable controller device (e.g., hand-held controller) that may or may not include a robotic system. The instrument driving mechanism may provide mechanical and electrical interface to the steerable catheter assembly 1220. The mechanical interface may allow the steerable catheter assembly 1220 to be releasably coupled to the instrument driving mechanism. For instance, a handle portion of the steerable catheter assembly can be attached to the instrument driving mechanism via quick install/release means, such as magnets, spring-loaded levels and the like. In some cases, the steerable catheter assembly may be coupled to or released from the instrument driving mechanism manually without using a tool.

The steerable catheter assembly 1220 may comprise a handle portion 1223 that may include components configured to processing image data, provide power, or establish communication with other external devices. For instance, the handle portion 1223 may include a circuitry and communication elements that enables electrical communication between the steerable catheter assembly 1220 and the instrument driving mechanism 1213, and any other external system or devices. In another example, the handle portion 1223 may comprise circuitry elements such as power sources for powering the electronics (e.g., camera and LED lights) of the endoscope. In some cases, the handle portion may be in electrical communication with the instrument driving mechanism 1213 via an electrical interface (e.g., printed circuit board) so that image/video data and/or sensor data can be received by the communication module of the instrument driving mechanism and may be transmitted to other external devices/systems. Alternatively or in addition to, the instrument driving mechanism 1213 may provide a mechanical interface only. The handle portion may be in electrical communication with a modular wireless communication device or any other user device (e.g., portable/hand-held device or controller) for transmitting sensor data and/or receiving control signals. Details about the handle portion are described later herein.

The steerable catheter assembly 1220 may comprise a flexible elongate member 1211 that is coupled to the handle portion. In some embodiments, the flexible elongate member may comprise a shaft, steerable tip and a steerable section. The steerable catheter assembly may be a single use robotic bronchoscope. In some cases, only the elongate member may be disposable. In some cases, at least a portion of the elongate member (e.g., shaft, steerable tip, etc.) may be disposable. In some cases, the entire steerable catheter assembly 1220 including the handle portion and the elongate member can be disposable. The flexible elongate member and the handle portion are designed such that the entire steerable catheter assembly can be disposed of at low cost. Details about the flexible elongate member and the steerable catheter assembly are described later herein.

In some embodiments, the provided bronchoscope system may also comprise a user interface. As illustrated in the example system 1230, the bronchoscope system may include a treatment interface module 1231 (user console side) and/or a treatment control module 1233 (patient and robot side). The treatment interface module may allow an operator or user to interact with the bronchoscope during surgical procedures. In some embodiments, the treatment control module 1233 may be a hand-held controller. The treatment control module may, in some cases, comprise a proprietary user input device and one or more add-on elements removably coupled to an existing user device to improve user input experience. For instance, physical track-ball or roller can replace or supplement the function of at least one of the virtual graphical element (e.g., navigational arrow displayed on touchpad) displayed on a graphical user interface (GUI) by giving it similar functionality to the graphical element which it replaces. Examples of user devices may include, but are not limited to, mobile devices, smartphones/cellphones, tablets, personal digital assistants (PDAs), laptop or notebook computers, desktop computers, media content players, and the like. Details about the user interface device and user console are described later herein.

The user console 1231 may be mounted to the robotic support system 1210. Alternatively or in addition to, the user console or a portion of the user console (e.g., treatment interface module) may be mounted to a separate mobile cart.

Figure 13:
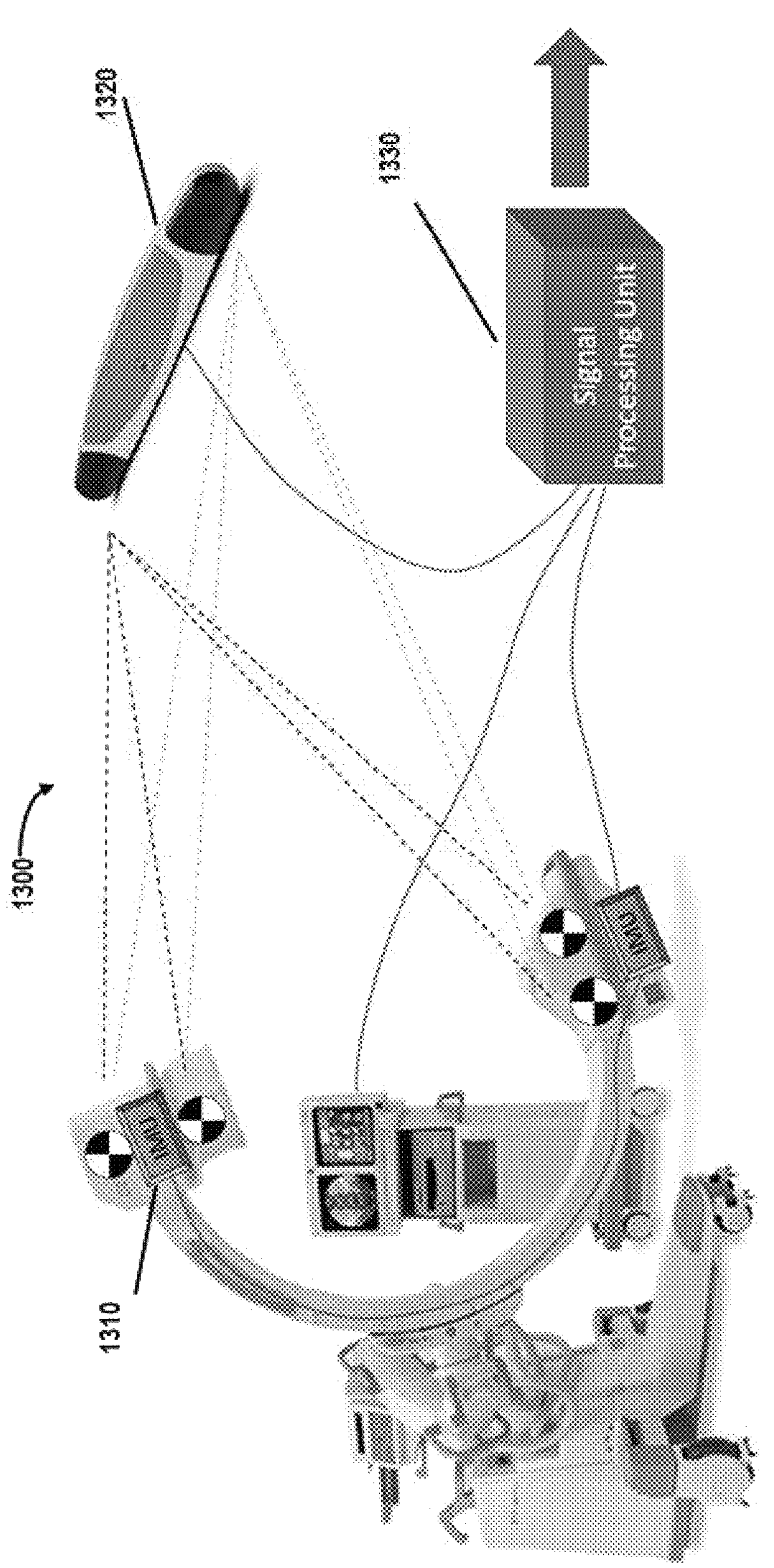
FIG. 13 shows an example of a fluoroscopy (tomosynthesis) imaging system.

The present disclosure provides a robotic endoluminal platform with integrated tool-in-lesion tomosynthesis technology. In some cases, the robotic endoluminal platform may be a bronchoscopy platform. The platform may be configured to perform one or more operations consistent with the method described herein. FIG. 13 shows an example of a robotic endoluminal platform and its components or subsystems, in accordance with some embodiments of the invention. In some embodiments, the platform may comprise a robotic bronchoscopy system and one or more subsystems that can be used in combination with the robotic bronchoscopy system of the present disclosure.

In some embodiments, the one or more subsystems may include imaging systems such as a fluoroscopy imaging system for providing real-time imaging of a target site (e.g., comprising lesion). Multiple 2D fluoroscopy images may be used to create tomosynthesis or Cone Beam CT (CBCT) reconstruction to better visualize and provide 3D coordinates of the anatomical structures. FIG. 13 shows an example of a fluoroscopy (tomosynthesis) imaging system 1300. For example, the fluoroscopy (tomosynthesis) imaging system may perform accurate lesion location tracking or tool-in-lesion confirmation before or during surgical procedure as described above. In some cases, lesion location may be tracked based on location data about the fluoroscopy (tomosynthesis) imaging system/station (e.g., C arm) and image data captured by the fluoroscopy (tomosynthesis) imaging system. The lesion location may be registered with the coordinate frame of the robotic bronchoscopy system.

In some cases, a location, pose or motion of the fluoroscopy imaging system may be measured/estimated to register the coordinate frame of the image to the robotic bronchoscopy system, or for constructing the 3D model/image. The pose or motion of the fluoroscopy (tomosynthesis) imaging system may be measured using any suitable motion/location sensors 1310 disposed on the fluoroscopy (tomosynthesis) imaging system. The motion/location sensors may include, for example, inertial measurement units (IMUs)), one or more gyroscopes, velocity sensors, accelerometers, magnetometers, location sensors (e.g., global positioning system (GPS) sensors), vision sensors (e.g., imaging devices capable of detecting visible, infrared, or ultraviolet light, such as cameras), proximity or range sensors (e.g., ultrasonic sensors, lidar, time-of-flight or depth cameras), altitude sensors, attitude sensors (e.g., compasses) and/or field sensors (e.g., magnetometers, electromagnetic sensors, radio sensors). In some cases, the one or more sensors for tracking the motion and location of the fluoroscopy (tomosynthesis) imaging station may be disposed on the imaging station or be located remotely from the imaging station, such as a wall-mounted camera 1320. The C-arm fluoroscopy (tomosynthesis) imaging system in different (rotation) poses while taking images of a subject. The various poses may be captured by the one or more sensors as described above.

Figure 21:
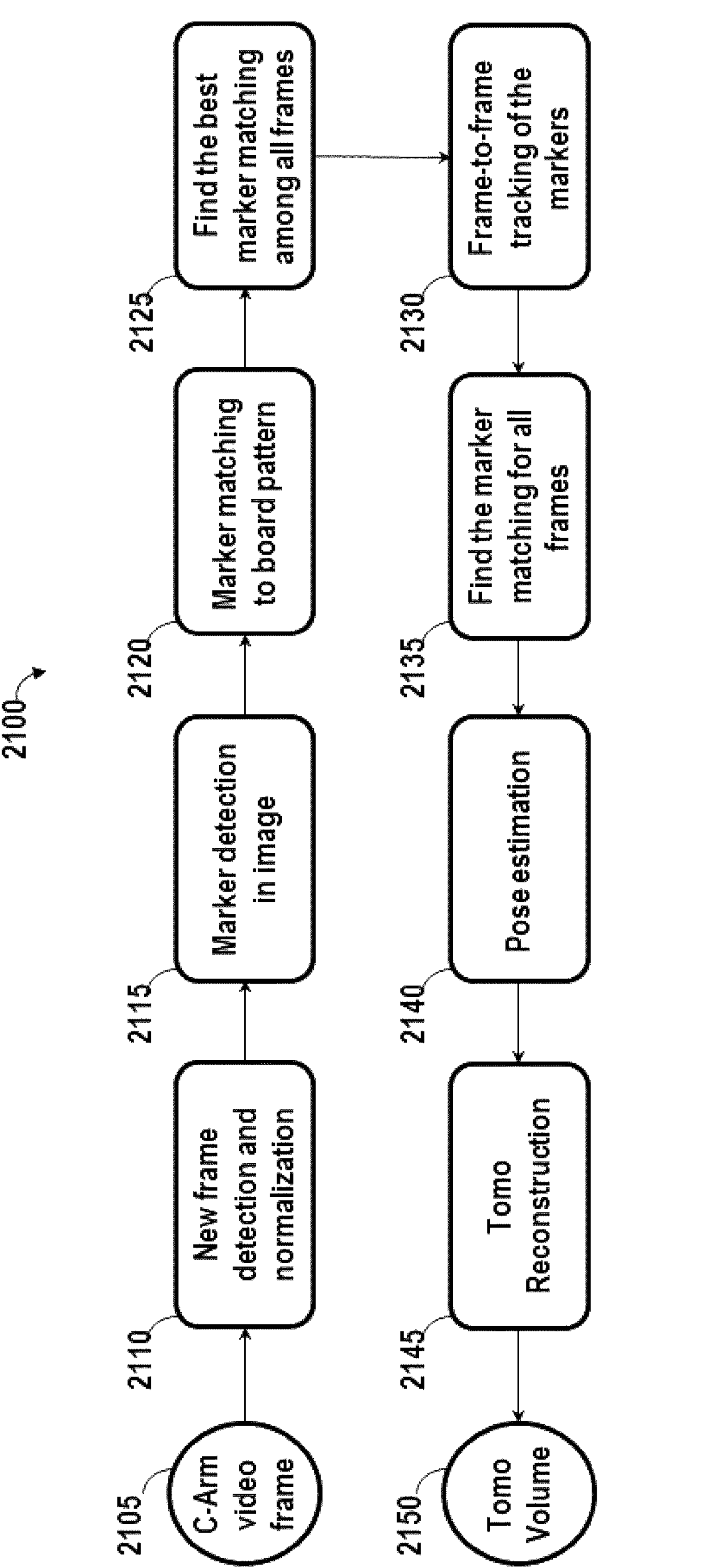
FIG. 21 shows an example process of tomosynthesis image reconstruction.

In some cases, the pose of the C-arm fluoroscopy (tomosynthesis) imaging system may be estimated using optical method. FIG. 21 shows an example process 2100 of tomosynthesis image reconstruction. In some cases, the tomosynthesis image reconstruction of the process 2100 may comprise generating a 3D volume with a combination of X-ray projections images acquired at different angles (acquired by any type of C-arm systems The process may comprise obtaining C-arm video or imaging data using an imaging apparatus such as C-arm imaging system 105. The C-arm imaging system may comprise a source (e.g., an X-ray source) and a detector (e.g., an X-ray detector or X-ray imager). The C-arm system may generate video or imaging data that can be utilized for both tomosynthesis and augmented fluoroscopy (e.g., display of live 2D fluoroscopy augmented with overlay of lesion, tool or other information). In some cases, the raw video frames may be used for both tomosynthesis and fluoroscopy. However, tomosynthesis may require unique frames from the C-arm, while augmented fluoroscopy may operate using duplicate frames from the C-arm as it is live video, the methods herein may provide a unique frame checking algorithm such that the video frames for tomosynthesis are processed to ensure uniqueness. For example, upon receiving a new image frame, if the current mode is tomosynthesis, the image frame may be processed to determine whether it is a unique frame or a duplicate. The uniqueness check may be based on image intensity comparison threshold. For example, when the intensity difference against a previous frame is below a predetermine threshold, the frame may be identified as a duplicate frame and may be removed from being used for tomosynthesis reconstruction. If the current mode is fluoroscopy, the image frame may not be processed for checking uniqueness.

The operation 2110 may comprise detecting the video or imaging frames from the C-arm source and the video or imaging frames may be normalized. Normalization may be an image processing technique that changes the range of pixel intensity values in the video or imaging frames. In general, normalization may transform an n-dimension gray-scale image $I:\{X \subseteq R^n\} \rightarrow \{Min, \ldots, Max\}$ with intensity values in the range (Min, Max) into a new image $I_{NEW}: \{X \subseteq R^n\} \rightarrow \{Min_{NEW}, \ldots, Max_{NEW}\}$ with intensity values in the range ($Min_{NEW}$, $Max_{NEW}$). Examples of possible normalization techniques that may be applied to the C-arm video or image frames, may include linear scaling, clipping, log scaling, z-score, or any other suitable types of normalization.

Accurate camera pose and camera parameters is important for both tomosynthesis image reconstruction and augmented fluoroscopy overlay. In some cases, the marker detection may be performed 2115 for pose estimation. In some examples, the markers may be 2D or 3D markers on a tomosynthesis board such that X-ray projections of markers on the tomosynthesis board may be markers to be detected in the X-ray image. The markers may be detected using any suitable image processing or computer vision techniques (e.g., structure from motion). For example, OpenCV's blob detection algorithm may be used to detect markers that are blob-shaped. In some cases, the detected markers (e.g., blobs) may be detected to have certain properties, such as position, shape, size, color, darkness/lightness, opacity, or other suitable properties of markers.

In some cases, the method 2100 may comprise matching markers to a board pattern at 2120. The markers detected in the fluoroscopic image may be matched to the tomosynthesis board. As described above, the markers may exhibit any number of various physical properties (e.g., position, shape, size, color, darkness/lightness, opacity, etc.) that may be detected and may be used for matching the markers to the marker pattern on the tomosynthesis board. For example, the tomosynthesis board may have different types of markers such as large blobs and small blobs. In some cases, the large blobs and small blobs may create a pattern which may be used to match the marker pattern in the video or image frames to the pattern on the tomosynthesis board.

In some cases, the method 2100 may comprise finding the best marker matching across all video or image frames 2125. The initial marker matching may be the match between markers in the frames and the tomosynthesis board. In some cases, the pattern of the matched markers may be compared over the tomosynthesis board to find the best matching using the Hamming distance. For each frame, the matching with a pattern matching score (e.g., number of matched markers divided by total number of detected markers) may be obtained. The best match may be determined as the match with the highest pattern matching score among all the frames 2125.

The process 2100 may perform frame-to-frame tracking 2130. At a high level, the frame-to-frame tracking 2130 may include propagating the marker matching from the best match determined at operation 2125 to the rest of the tomosynthesis video and image frames by robust tomosynthesis marker tracking. In some cases, (i) the markers in a pair of consecutive frames may be initially matched; (ii) each marker in the first frame may then be matched to the k-nearest markers in a second frame; (iii) for each matched pair of markers, a motion displacement between two frames may be computed; (iv) all the markers in the first frame may be transferred to the second frame with the motion displacement; (v) if the motion displacement between a given transferred point from the first frame and a given point location in the second frame is smaller than a threshold, and the two given marker types are the same, then this match may be an inlier; (vi) the best matching may be the motion with the most inliers. From the computed tomosynthesis marker tracking 2130, the existing marker matches in the current frame are transferred to the marker matches in the next frame. In some cases, such process may be repeated for all frames 2135, finding the marker matches for all frames, where the markers in all frames are matched to the tomosynthesis board.

In some cases, the imaging device pose estimation 2140 may comprise recovering rotation and translation by minimizing the reprojection error from 3D-2D point correspondences to perform the pose estimation. In some cases, Perspective-n-Point (PnP) pose computation may be used to recover the camera poses from n pairs of point correspondences. The minimal form of PnP problem may be P3P and may be solved with three point correspondences. For each tomosynthesis frame, there may be multiple marker matches, and a RANSAC variant of PnP solver may be used for pose estimation. In some cases, the pose estimation 2140 may be further refined by minimizing the reprojection error using a non-linear minimization method and starting from the initial pose estimate with the PnP solver.

The tomosynthesis reconstruction 2145 may be based on the pose estimation result. In some cases, the tomosynthesis reconstruction 2145 may be implemented as a model in Python (or other suitable programming languages) using the open-source ASTRA (a MATLAB and Python toolbox of high-performance GPU primitives for 2D and 3D tomography) toolbox (or other suitable toolboxes or packages). In the tomosynthesis reconstruction, input to the model may be as follows: (i) undistorted and inpainted (inpainting: a process to restore damaged image) projection images; (ii) estimated projection matrices, such as poses of each projection; and (iii) size, resolution and estimated position of the targeted tomosynthesis reconstruction volume. The output of the model is the tomosynthesis reconstruction (e.g., volume in NifTI format) 2145. For example, the tomosynthesis reconstruction may include a 3D-volume data of the surgical field or target scene with the lesion and tool visible within the 3D-volume data Referring back to FIG. 13, in some embodiments, a location of lesion may be segmented in the image data (e.g., 3D-volume data) captured by the fluoroscopy (tomosynthesis) imaging system with aid of a signal processing unit 1330. One or more processors of the signal processing unit may be configured to further overlay treatment locations (e.g., lesion) on the real-time fluoroscopic image/video. For example, the processing unit may be configured to generate an augmented layer comprising augmented information such as the location of the treatment location or target site. In some cases, the augmented layer may also comprise graphical marker indicating a path to this target site. The augmented layer may be a substantially transparent image layer comprising one or more graphical elements (e.g., box, arrow, etc.). The augmented layer may be superposed onto the optical view of the optical images or video stream captured by the fluoroscopy (tomosynthesis) imaging system, and/or displayed on the display device. The transparency of the augmented layer allows the optical image to be viewed by a user with graphical elements overlay on top of. In some cases, both the segmented lesion images and an optimum path for navigation of the elongate member to reach the lesion may be overlaid onto the real time tomosynthesis images. This may allow operators or users to visualize the accurate location of the lesion as well as a planned path of the bronchoscope movement. In some cases, the segmented and reconstructed images (e.g., CT images as described elsewhere) provided prior to the operation of the systems described herein may be overlaid on the real time images.

In some embodiments, the one or more subsystems of the platform may comprise one or more treatment subsystems such as manual or robotic instruments (e.g., biopsy needles, biopsy forceps, biopsy brushes) and/or manual or robotic therapeutical instruments (e.g., RF ablation instrument, Cryo instrument, Microwave instrument, and the like).

In some embodiments, the one or more subsystems of the platform may comprise a navigation and localization subsystem. The navigation and localization subsystem may be configured to construct a virtual airway model based on the pre-operative image (e.g., pre-op CT image or tomosynthesis). The navigation and localization subsystem may be configured to identify the segmented lesion location in the 3D rendered airway model and based on the location of the lesion, the navigation and localization subsystem may generate an optimal path from the main bronchi to the lesions with a recommended approaching angle towards the lesion for performing surgical procedures (e.g., biopsy).

At a registration step before driving the bronchoscope to the target site, the system may align the rendered virtual view of the airways to the patient airways. Image registration may consist of a single registration step or a combination of a single registration step and real-time sensory updates to registration information. The registration process may include finding a transformation that aligns an object (e.g., airway model, anatomical site) between different coordinate systems (e.g., EM sensor coordinates and patient 3D model coordinates based on pre-operative CT imaging). Details about the registration are described later herein.

Once registered, all airways may be aligned to the pre-operative rendered airways. During robotic bronchoscope driving towards the target site, the location of the bronchoscope inside the airways may be tracked and displayed. In some cases, location of the bronchoscope with respect to the airways may be tracked using positioning sensors. Other types of sensors (e.g., camera) can also be used instead of or in conjunction with the positioning sensors using sensor fusion techniques. Positioning sensors such as electromagnetic (EM) sensors may be embedded at the distal tip of the catheter and an EM field generator may be positioned next to the patient torso during procedure. The EM field generator may locate the EM sensor position in 3D space or may locate the EM sensor position and orientation in 5D or 6D space. This may provide a visual guide to an operator when driving the bronchoscope towards the target site.

In real-time EM tracking, the EM sensor comprising of one or more sensor coils embedded in one or more locations and orientations in the medical instrument (e.g., tip of the endoscopic tool) measures the variation in the EM field created by one or more static EM field generators positioned at a location close to a patient. The location information detected by the EM sensors is stored as EM data. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively registered to the patient anatomy (e.g., 3D model) in order to determine the registration transformation that aligns a single location in the coordinate system with a position in the pre-operative model of the patient's anatomy.

In some embodiments, the platform herein may utilize fluoroscopic imaging systems to determine the location and orientation of medical instruments and patient anatomy within the coordinate system of the surgical environment. In particular, the systems and methods herein may employ a mobile C-arm fluoroscopy as a low-cost and mobile real-time qualitative assessment tool. Fluoroscopy is an imaging modality that obtains real-time moving images of patient anatomy, and medical instruments. Fluoroscopic systems may include C-arm systems which provide positional flexibility and are capable of orbital, horizontal, and/or vertical movement via manual or automated control. Fluoroscopic image data from multiple viewpoints (i.e., with the fluoroscopic imager moved among multiple locations) in the surgical environment may be compiled to generate two-dimensional or three-dimensional tomographic images. When using a fluoroscopic imager system that include a digital detector (e.g., a flat panel detector), the generated and compiled fluoroscopic image data may permit the sectioning of planar images in parallel planes according to tomosynthesis imaging techniques. The C-arm imaging system may comprise a source (e.g., an X-ray source) and a detector (e.g., an X-ray detector or X-ray imager). The X-ray detector may generate an image representing the intensities of received x-rays. The imaging system may reconstruct 3D image based on multiple 2D image acquired from a wide range of angels. In some cases, the rotation angle range may be at least 120-degree, 130-degree, 140-degree, 150-degree, 160-degree, 170-degree, 180-degree or greater. In some cases, the 3D image may be generated based on a pose of the X-ray imager.

Figure 14:
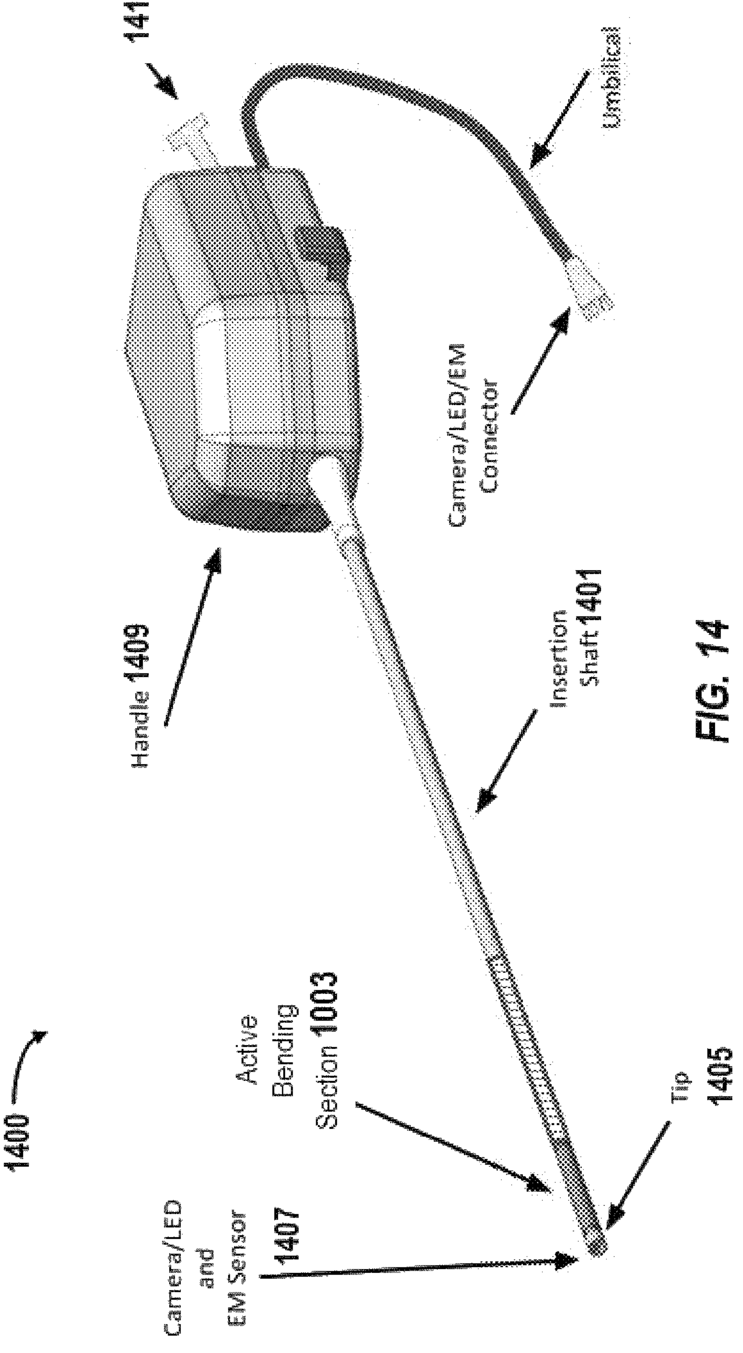
FIG. 14 and FIG. 15 show examples of a flexible endoscope.

The bronchoscope or the catheter may be disposable. FIG. 14 illustrates an example of a flexible endoscope 1400, in accordance with some embodiments of the present disclosure. As shown in FIG. 14, the flexible endoscope 1400 may comprise a handle/proximal portion 1409 and a flexible elongate member to be inserted inside of a subject. The flexible elongate member can be the same as the one described above. In some embodiments, the flexible elongate member may comprise a proximal shaft (e.g., insertion shaft 1401), steerable tip (e.g., tip 1405), and a steerable section (active bending section 1403). The active bending section, and the proximal shaft section can be the same as those described elsewhere herein. The endoscope 1400 may also be referred to as steerable catheter assembly as described elsewhere herein. In some cases, the endoscope 1400 may be a single-use robotic endoscope. In some cases, the entire catheter assembly may be disposable. In some cases, at least a portion of the catheter assembly may be disposable. In some cases, the entire endoscope may be released from an instrument driving mechanism and can be disposed of. In some embodiment, the endoscope may contain varying levels of stiffness along the shaft, as to improve functional operation.

The endoscope or steerable catheter assembly 1400 may comprise a handle portion 1409 that may include one or more components configured to process image data, provide power, or establish communication with other external devices. For instance, the handle portion may include a circuitry and communication elements that enables electrical communication between the steerable catheter assembly 1400 and an instrument driving mechanism (not shown), and any other external system or devices. In another example, the handle portion 1409 may comprise circuitry elements such as power sources for powering the electronics (e.g., camera, electromagnetic sensor and LED lights) of the endoscope.

The one or more components located at the handle may be optimized such that expensive and complicated components may be allocated to the robotic support system, a hand-held controller or an instrument driving mechanism thereby reducing the cost and simplifying the design the disposable endoscope. The handle portion or proximal portion may provide an electrical and mechanical interface to allow for electrical communication and mechanical communication with the instrument driving mechanism. The instrument driving mechanism may comprise a set of motors that are actuated to rotationally drive a set of pull wires of the catheter. The handle portion of the catheter assembly may be mounted onto the instrument drive mechanism so that its pulley/capstans assemblies are driven by the set of motors. The number of pulleys may vary based on the pull wire configurations. In some cases, one, two, three, four, or more pull wires may be utilized for articulating the flexible endoscope or catheter.

The handle portion may be designed allowing the robotic bronchoscope to be disposable at reduced cost. For instance, classic manual and robotic bronchoscopes may have a cable in the proximal end of the bronchoscope handle. The cable often includes illumination fibers, camera video cable, and other sensors fibers or cables such as electromagnetic (EM) sensors, or shape sensing fibers. Such complex cable can be expensive adding to the cost of the bronchoscope. The provided robotic bronchoscope may have an optimized design such that simplified structures and components can be employed while preserving the mechanical and electrical functionalities. In some cases, the handle portion of the robotic bronchoscope may employ a cable-free design while providing a mechanical/electrical interface to the catheter.

The electrical interface (e.g., printed circuit board) may allow image/video data and/or sensor data to be received by the communication module of the instrument driving mechanism and may be transmitted to other external devices/systems. In some cases, the electrical interface may establish electrical communication without cables or wires. For example, the interface may comprise pins soldered onto an electronics board such as a printed circuit board (PCB). For instance, receptacle connector (e.g., the female connector) is provided on the instrument driving mechanism as the mating interface. This may beneficially allow the endoscope to be quickly plugged into the instrument driving mechanism or robotic support without utilizing extra cables. Such type of electrical interface may also serve as a mechanical interface such that when the handle portion is plugged into the instrument driving mechanism, both mechanical and electrical coupling is established. Alternatively or in addition to, the instrument driving mechanism may provide a mechanical interface only. The handle portion may be in electrical communication with a modular wireless communication device or any other user device (e.g., portable/hand-held device or controller) for transmitting sensor data and/or receiving control signals.

In some cases, the handle portion 1409 may comprise one or more mechanical control modules such as lure 1411 for interfacing the irrigation system/aspiration system. In some cases, the handle portion may include lever/knob for articulation control. Alternatively, the articulation control may be located at a separate controller attached to the handle portion via the instrument driving mechanism.

The endoscope may be attached to a robotic support system or a hand-held controller via the instrument driving mechanism. The instrument driving mechanism may be provided by any suitable controller device (e.g., hand-held controller) that may or may not include a robotic system. The instrument driving mechanism may provide mechanical and electrical interface to the steerable catheter assembly 1400. The mechanical interface may allow the steerable catheter assembly 1400 to be releasably coupled to the instrument driving mechanism. For instance, the handle portion of the steerable catheter assembly can be attached to the instrument driving mechanism via quick install/release means, such as magnets, spring-loaded levels and the like. In some cases, the steerable catheter assembly may be coupled to or released from the instrument driving mechanism manually without using a tool.

In the illustrated example, the distal tip of the catheter or endoscope shaft is configured to be articulated/bent in two or more degrees of freedom to provide a desired camera view or control the direction of the endoscope. As illustrated in the example, imaging device (e.g., camera), position sensors (e.g., electromagnetic sensor) 1407 is located at the tip of the catheter or endoscope shaft 1405. For example, line of sight of the camera may be controlled by controlling the articulation of the active bending section 1403. In some instances, the angle of the camera may be adjustable such that the line of sight can be adjusted without or in addition to articulating the distal tip of the catheter or endoscope shaft. For example, the camera may be oriented at an angle (e.g., tilt) with respect to the axial direction of the tip of the endoscope with aid of an optimal component.

The distal tip 1405 may be a rigid component that allow for positioning sensors such as electromagnetic (EM) sensors, imaging devices (e.g., camera) and other electronic components (e.g., LED light source) being embedded at the distal tip.

In real-time EM tracking, the EM sensor comprising of one or more sensor coils embedded in one or more locations and orientations in the medical instrument (e.g., tip of the endoscopic tool) measures the variation in the EM field created by one or more static EM field generators positioned at a location close to a patient. The location information detected by the EM sensors is stored as EM data. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. For example, the EM field generator may be positioned close to the patient torso during procedure to locate the EM sensor position in 3D space or may locate the EM sensor position and orientation in 5D or 6D space. This may provide a visual guide to an operator when driving the bronchoscope towards the target site.

The endoscope may have a unique design in the elongate member. In some cases, the active bending section 1403, and the proximal shaft of the endoscope may consist of a single tube that incorporates a series of cuts (e.g., reliefs, slits, etc.) along its length to allow for improved flexibility, a desirable stiffness as well as the anti-prolapse feature (e.g., features to define a minimum bend radius).

As described above, the active bending section 1403 may be designed to allow for bending in two or more degrees of freedom (e.g., articulation). A greater bending degree such as 180 and 270 degrees (or other articulation parameters for clinical indications) can be achieved by the unique structure of the active bending section. In some cases, a variable minimum bend radius along the axial axis of the elongate member may be provided such that an active bending section may comprise two or more different minimum bend radii.

The articulation of the endoscope may be controlled by applying force to the distal end of the endoscope via one or multiple pull wires. The one or more pull wires may be attached to the distal end of the endoscope. In the case of multiple pull wires, pulling one wire at a time may change the orientation of the distal tip to pitch up, down, left, right or any direction needed. In some cases, the pull wires may be anchored at the distal tip of the endoscope, running through the bending section, and entering the handle where they are coupled to a driving component (e.g., pulley). This handle pulley may interact with an output shaft from the robotic system.

In some embodiments, the proximal end or portion of one or more pull wires may be operatively coupled to various mechanisms (e.g., gears, pulleys, capstans, etc.) in the handle portion of the catheter assembly. The pull wire may be a metallic wire, cable or thread, or it may be a polymeric wire, cable or thread. The pull wire can also be made of natural or organic materials or fibers. The pull wire can be any type of suitable wire, cable or thread capable of supporting various kinds of loads without deformation, significant deformation, or breakage. The distal end/portion of one or more pull wires may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

The pull wires may be made of any suitable material such as stainless steel (e.g., SS316), metals, alloys, polymers, nylons or biocompatible material. Pull wires may be a wire, cable or a thread. In some embodiments, different pull wires may be made of different materials for varying the load bearing capabilities of the pull wires. In some embodiments, different sections of the pull wires may be made of different material to vary the stiffness and/or load bearing along the pull. In some embodiments, pull wires may be utilized for the transfer of electrical signals.

The proximal design may improve the reliability of the device without introducing extra cost allowing for a low-cost single-use endoscope. In another aspect of the invention, a single-use robotic endoscope is provided. The robotic endoscope may be a bronchoscope and can be the same as the steerable catheter assembly as described elsewhere herein. Traditional endoscopes can be complex in design and are usually designed to be reused after procedures, which require thorough cleaning, dis-infection, or sterilization after each procedure. The existing endoscopes are often designed with complex structures to ensure the endoscopes can endure the cleaning, dis-infection, and sterilization processes. The provided robotic bronchoscope can be a single-use endoscope that may beneficially reduce cross-contamination between patients and infections. In some cases, the robotic bronchoscope may be delivered to the medical practitioner in a pre-sterilized package and are intended to be disposed of after a single-use.

Figure 15:
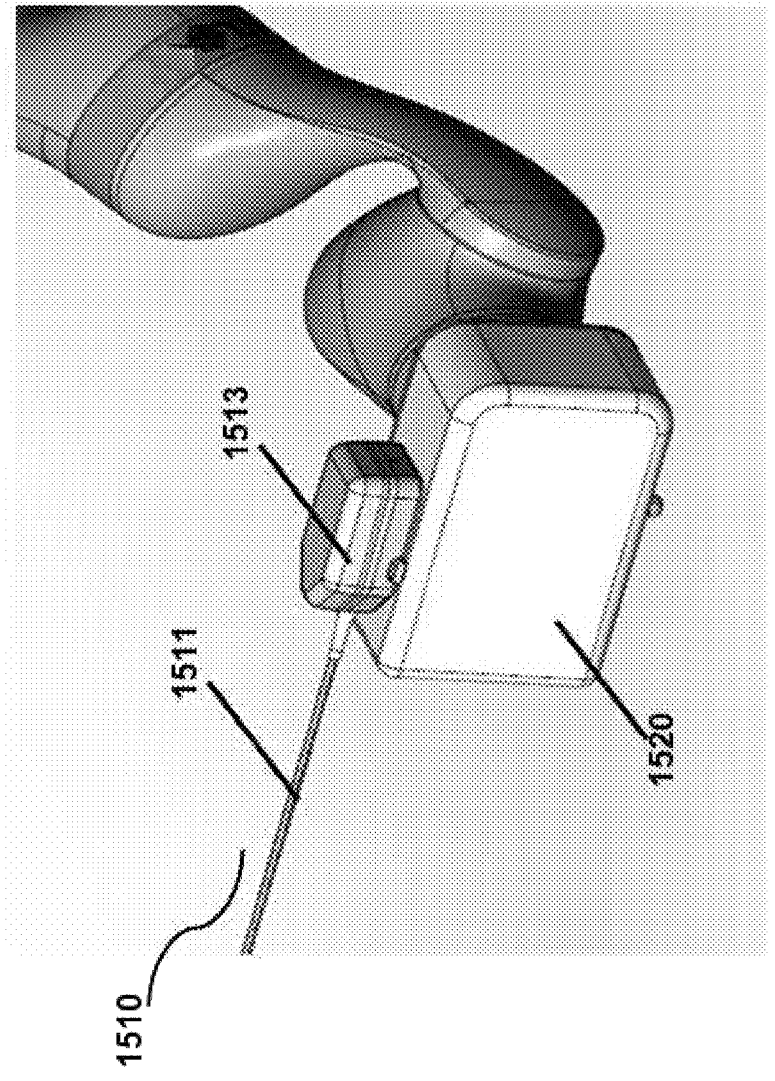

As shown in FIG. 15, a robotic bronchoscope 1510 may comprise a handle portion 1513 and a flexible elongate member 1511. In some embodiments, the flexible elongate member 1111 may comprise a shaft, steerable tip, and a steerable/active bending section. The robotic bronchoscope 1510 can be the same as the steerable catheter assembly as described in FIG. 14. The robotic bronchoscope may be a single-use robotic endoscope. In some cases, only the catheter may be disposable. In some cases, at least a portion of the catheter may be disposable. In some cases, the entire robotic bronchoscope may be released from the instrument driving mechanism and can be disposed of. In some cases, the bronchoscope may contain varying levels of stiffness along its shaft, as to improve functional operation. In some cases, a minimum bend radius along the shaft may vary.

The robotic bronchoscope can be releasably coupled to an instrument driving mechanism 1520. The instrument driving mechanism 1520 may be mounted to the arm of the robotic support system or to any actuated support system as described elsewhere herein. The instrument driving mechanism may provide mechanical and electrical interface to the robotic bronchoscope 1510. The mechanical interface may allow the robotic bronchoscope 1510 to be releasably coupled to the instrument driving mechanism. For instance, the handle portion of the robotic bronchoscope can be attached to the instrument driving mechanism via quick install/release means, such as magnets and spring-loaded levels. In some cases, the robotic bronchoscope may be coupled or released from the instrument driving mechanism manually without using a tool.

Figure 16:
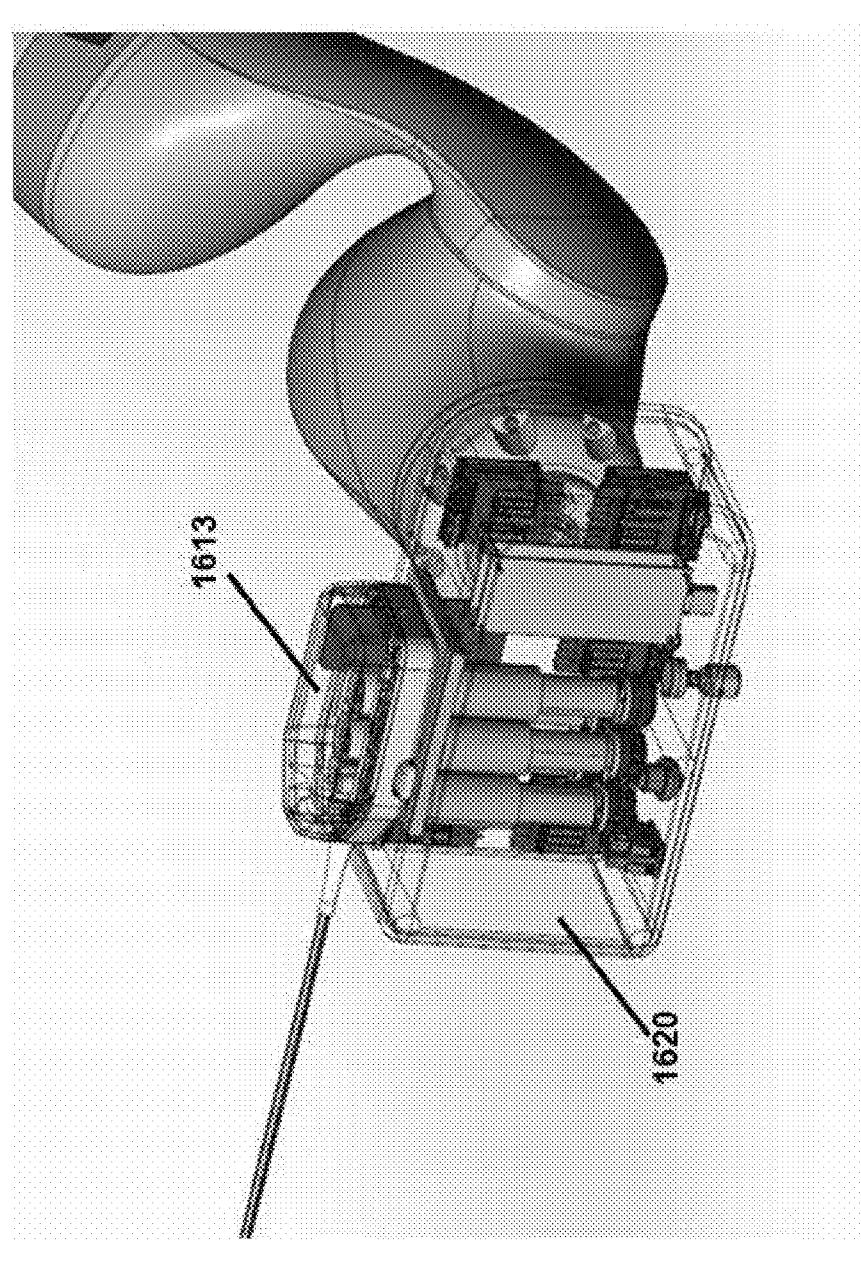
FIG. 16 shows an example of an instrument driving mechanism providing mechanical interface to the handle portion of a robotic bronchoscope.

FIG. 16 shows an example of an instrument driving mechanism 1620 providing mechanical interface to the handle portion 1613 of the robotic bronchoscope. As shown in the example, the instrument driving mechanism 1620 may comprise a set of motors that are actuated to rotationally drive a set of pull wires of the flexible endoscope or catheter. The handle portion 1613 of the catheter assembly may be mounted onto the instrument drive mechanism so that its pulley assemblies or capstans are driven by the set of motors. The number of pulleys may vary based on the pull wire configurations. In some cases, one, two, three, four, or more pull wires may be utilized for articulating the flexible endoscope or catheter.

The handle portion may be designed allowing the robotic bronchoscope to be disposable at reduced cost. For instance, classic manual and robotic bronchoscopes may have a cable in the proximal end of the bronchoscope handle. The cable often includes illumination fibers, camera video cable, and other sensors fibers or cables such as electromagnetic (EM) sensors, or shape sensing fibers. Such complex cable can be expensive, adding to the cost of the bronchoscope. The provided robotic bronchoscope may have an optimized design such that simplified structures and components can be employed while preserving the mechanical and electrical functionalities. In some cases, the handle portion of the robotic bronchoscope may employ a cable-free design while providing a mechanical/electrical interface to the catheter.

Figure 17:
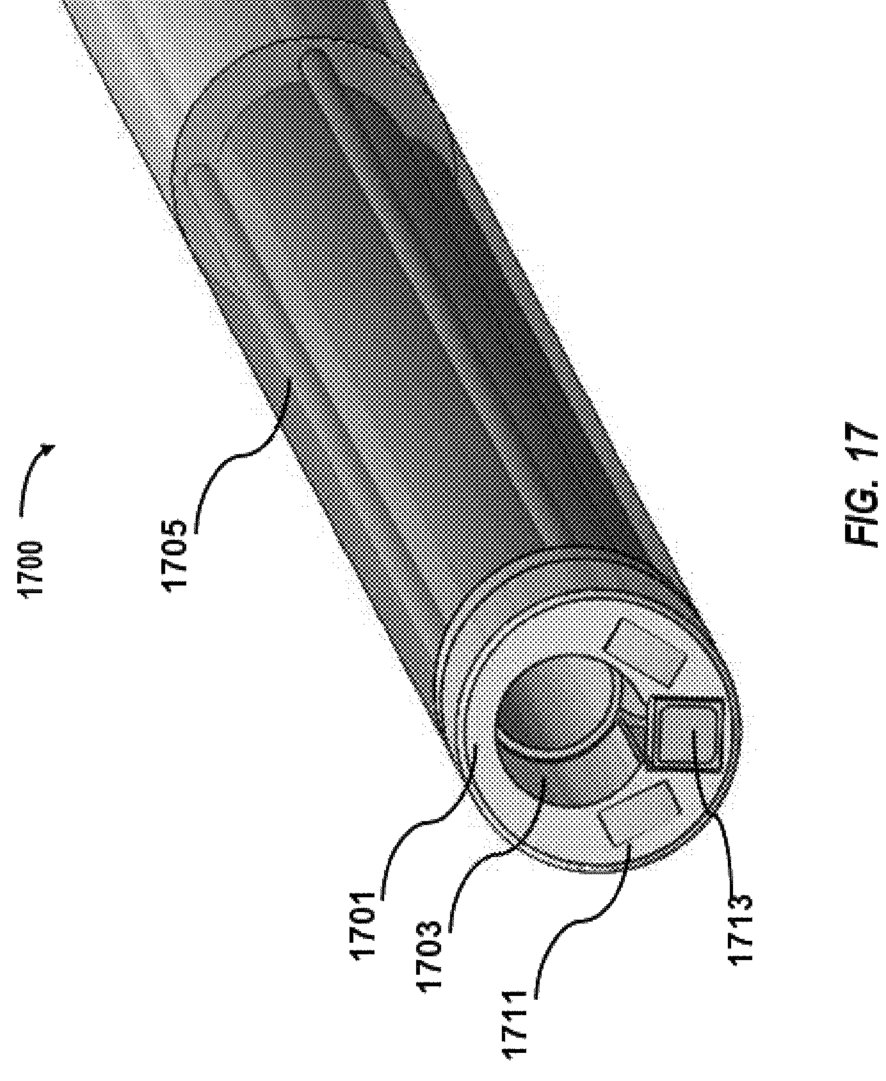
FIG. 17 shows an example of a distal tip of an endoscope.

FIG. 17 shows an example of a distal tip 1700 of an endoscope. In some cases, the distal portion or tip of the catheter 1700 may be substantially flexible such that it can be steered into one or more directions (e.g., pitch, yaw). The catheter may comprise a tip portion, bending section, and insertion shaft. In some embodiments, the catheter may have variable bending stiffness along the longitudinal axis direction. For instance, the catheter may comprise multiple sections having different bending stiffness (e.g., flexible, semi-rigid, and rigid). The bending stiffness may be varied by selecting materials with different stiffness/rigidity, varying structures in different segments (e.g., cuts, patterns), adding additional supporting components or any combination of the above. In some embodiments, the catheter may have variable minimum bend radius along the longitudinal axis direction. The selection of different minimum bend radius at different location long the catheter may beneficially provide anti-prolapse capability while still allow the catheter to reach hard-to-reach regions. In some cases, a proximal end of the catheter needs not be bent to a high degree thus the proximal portion of the catheter may be reinforced with additional mechanical structure (e.g., additional layers of materials) to achieve a greater bending stiffness. Such design may provide support and stability to the catheter. In some cases, the variable bending stiffness may be achieved by using different materials during extrusion of the catheter. This may advantageously allow for different stiffness levels along the shaft of the catheter in an extrusion manufacturing process without additional fastening or assembling of different materials.

The distal portion of the catheter may be steered by one or more pull wires 1705. The distal portion of the catheter may be made of any suitable material such as co-polymers, polymers, metals or alloys such that it can be bent by the pull wires. In some embodiments, the proximal end or terminal end of one or more pull wires 1705 may be coupled to a driving mechanism (e.g., gears, pulleys, capstan etc.) via the anchoring mechanism as described above.

The pull wire 1705 may be a metallic wire, cable or thread, or it may be a polymeric wire, cable or thread. The pull wire 1705 can also be made of natural or organic materials or fibers. The pull wire 1705 can be any type of suitable wire, cable or thread capable of supporting various kinds of loads without deformation, significant deformation, or breakage. The distal end or portion of one or more pull wires 1705 may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

The catheter may have a dimension so that one or more electronic components can be integrated to the catheter. For example, the outer diameter of the distal tip may be around 4 to 4.4 millimeters (mm), and the diameter of the working channel may be around 2 mm such that one or more electronic components can be embedded into the wall of the catheter. However, it should be noted that based on different applications, the outer diameter can be in any range smaller than 4 mm or greater than 4.4 mm, and the diameter of the working channel can be in any range according to the tool dimensional or specific application.

The one or more electronic components may comprise an imaging device, illumination device or sensors. In some embodiments, the imaging device may be a video camera 1713. The imaging device may comprise optical elements and image sensor for capturing image data. The image sensors may be configured to generate image data in response to wavelengths of light. A variety of image sensors may be employed for capturing image data such as complementary metal oxide semiconductor (CMOS) or charge-coupled device (CCD). The imaging device may be a low-cost camera. In some cases, the image sensor may be provided on a circuit board. The circuit board may be an imaging printed circuit board (PCB). The PCB may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors.

The illumination device may comprise one or more light sources 1711 positioned at the distal tip. The light source may be a light-emitting diode (LED), an organic LED (OLED), a quantum dot, or any other suitable light source. In some cases, the light source may be miniaturized LED for a compact design or Dual Tone Flash LED Lighting.

The imaging device and the illumination device may be integrated to the catheter. For example, the distal portion of the catheter may comprise suitable structures matching at least a dimension of the imaging device and the illumination device. The imaging device and the illumination device may be embedded into the catheter. FIG. 18 shows an example distal portion of the catheter with integrated imaging device and the illumination device. A camera may be located at the distal portion. The distal tip may have a structure to receive the camera, illumination device and/or the location sensor. For example, the camera may be embedded into a cavity 1810 at the distal tip of the catheter. The cavity 1810 may be integrally formed with the distal portion of the cavity and may have a dimension matching a length/width of the camera such that the camera may not move relative to the catheter. The camera may be adjacent to the working channel 1820 of the catheter to provide near field view of the tissue or the organs. In some cases, the attitude or orientation of the imaging device may be controlled by controlling a rotational movement (e.g., roll) of the catheter.

The power to the camera may be provided by a wired cable. In some cases, the cable wire may be in a wire bundle providing power to the camera as well as illumination elements or other circuitry at the distal tip of the catheter. The camera and/or light source may be supplied with power from a power source located at the handle portion via wires, copper wires, or via any other suitable means running through the length of the catheter. In some cases, real-time images or video of the tissue or organ may be transmitted to an external user interface or display wirelessly. The wireless communication may be WiFi, Bluetooth, RF communication or other forms of communication. In some cases, images or videos captured by the camera may be broadcasted to a plurality of devices or systems. In some cases, image and/or video data from the camera may be transmitted down the length of the catheter to the processors situated in the handle portion via wires, copper wires, or via any other suitable means. The image or video data may be transmitted via the wireless communication component in the handle portion to an external device/system. In some cases, the system may be designed such that no wires are visible or exposed to operators.

In conventional endoscopy, illumination light may be provided by fiber cables that transfer the light of a light source located at the proximal end of the endoscope, to the distal end of the robotic endoscope. In some embodiments of the disclosure, miniaturized LED lights may be employed and embedded into the distal portion of the catheter to reduce the design complexity. In some cases, the distal portion may comprise a structure 1430 having a dimension matching a dimension of the miniaturized LED light source. As shown in the illustrated example, two cavities 1430 may be integrally formed with the catheter to receive two LED light sources. For instance, the outer diameter of the distal tip may be around 4 to 4.4 millimeters (mm) and diameter of the working channel of the catheter may be around 2 mm such that two LED light sources may be embedded at the distal end. The outer diameter can be in any range smaller than 4 mm or greater than 4.4 mm, and the diameter of the working channel can be in any range according to the tool's dimensional or specific application. Any number of light sources may be included. The internal structure of the distal portion may be designed to fit any number of light sources.

In some cases, each of the LEDs may be connected to power wires which may run to the proximal handle. In some embodiment, the LEDs may be soldered to separated power wires that later bundle together to form a single strand. In some embodiments, the LEDs may be soldered to pull wires that supply power. In other embodiments, the LEDs may be crimped or connected directly to a single pair of power wires. In some cases, a protection layer such as a thin layer of biocompatible glue may be applied to the front surface of the LEDs to provide protection while allowing light emitted out. In some cases, an additional cover 1431 may be placed at the forwarding end face of the distal tip providing precise positioning of the LEDs as well as sufficient room for the glue. The cover 1831 may be composed of transparent material matching the refractive index of the glue so that the illumination light may not be obstructed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for navigating a robotic endoscopic apparatus, the method comprising:

(a) navigating the robotic endoscopic apparatus to a target region within a subject;

(b) acquiring a plurality of fluoroscopic images at different angles using a fluoroscopic imager when a tool is extended through the robotic endoscopic apparatus into the target region, and reconstructing a 3D fluoroscopic image based on the plurality of fluoroscopic images;

(c) identifying, from the 3D fluoroscopic image reconstructed in (b), a first slice with a first coordinate corresponding to a center of the target region in a depth direction, and identifying, from the 3D fluoroscopic image reconstructed in (b), a second slice with a second coordinate corresponding to the tool in the depth direction; and (d) determining whether the tool is inside the target region based at least in part on a comparison of a difference between the first coordinate and the second coordinate to a threshold, wherein the target region comprises a lesion that is visible in the 3D fluoroscopic image, wherein the threshold is determined based at least in part on a dimension of the lesion and wherein the dimension of the lesion is calculated based at least in part on a 3D model of the lesion obtained from an image acquired prior to (a).

2. The method of claim 1, wherein the first slice is identified by i) displaying the 3D fluoroscopic image within a graphical user interface (GUI), ii) selecting the first slice from a stack of slices when the lesion is in focus.

3. The method of claim 2, wherein the second slice is identified when the tool is in focus.

4. The method of claim 1, wherein the first slice or second slice is automatically identified based on a sharpness metric or contrast metric of each slice in the depth direction.

5. The method of claim 1, further comprising displaying the 3D fluoroscopic image within a graphical user interface (GUI) and displaying an overlay of the lesion on each slice from a plurality of stacks in the depth direction.

6. The method of claim 5, wherein the overlay is generated based at least in part on a 3D model of the lesion intersecting each slice.

7. The method of claim 5, further comprising determining whether the tool is inside the target region by identifying whether the overlay of the lesion appears in the second slice.

8. The method of claim 1, further comprising displaying, on a graphical user interface (GUI), the 3D fluoroscopic image, a first graphical visual indicator representing the first coordinate and a second graphical visual indicator representing the second coordinate.

9. The method of claim 1, wherein the 3D fluoroscopic image is reconstructed based on a pose of the fluoroscopic imager.

10. The method of claim 9, wherein the pose of the fluoroscopic imager is estimated based on markers contained in the acquired plurality of fluoroscopic images.

11. The method of claim 9, wherein the pose of the fluoroscopic imager is obtained based on location sensor data.

12. The method of claim 1, wherein the threshold comprises a margin and wherein the margin is determined based on empirical data.

13. A non-transitory computer-readable storage medium including instructions that, when executed by one or more processors, cause the one or more processors to perform operations comprising:

(a) navigating a robotic endoscopic apparatus to a target region within a subject;

(b) acquiring a plurality of fluoroscopic images at different angles using a fluoroscopic imager when a tool is extended through the robotic endoscopic apparatus into the target region, and reconstructing a 3D fluoroscopic image based on the plurality of fluoroscopic images;

(c) identifying, from the 3D fluoroscopic image reconstructed in (b), a first slice with a first coordinate corresponding to a center of the target region in a depth direction, and identifying, from the 3D fluoroscopic image reconstructed in (b), a second slice with a second coordinate corresponding to the tool in the depth direction; and (d) determining whether the tool is inside the target region based at least in part on a comparison of a difference between the first coordinate and the second coordinate to a threshold, wherein the target region comprises a lesion that is visible in the 3D fluoroscopic image, wherein the threshold is determined based at least in part on a dimension of the lesion and wherein the dimension of the lesion is calculated based at least in part on a 3D model of the lesion obtained from an image acquired prior to (a).

14. The non-transitory computer-readable storage medium of claim 13, wherein the first slice is identified by i) displaying the 3D fluoroscopic image within a graphical user interface (GUI), ii) selecting the first slice from a stack of slices when the lesion is in focus.

15. The non-transitory computer-readable storage medium of claim 14, wherein the second slice is identified when the tool is in focus.

* * * * *